US011950783B2

(12) United States Patent
Sgroi, Jr. et al.

(10) Patent No.: US 11,950,783 B2
(45) Date of Patent: *Apr. 9, 2024

(54) END EFFECTOR FORCE MEASUREMENT WITH DIGITAL DRIVE CIRCUIT

(71) Applicant: Covidien LP, Mansfield, MA (US)

(72) Inventors: Anthony Sgroi, Jr., Southbury, CT (US); David Valentine, Jr., Hamden, CT (US); Ramiro Cabrera, Cheshire, CT (US); Ethan Collins, Naugatuck, CT (US); Scott Firth, Guilford, CT (US); Joseph Eisinger, Northford, CT (US); John J. Hryb, IV, Southington, CT (US); Patrick Mozdzierz, Glastonbury, CT (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/857,274

(22) Filed: Jul. 5, 2022

(65) Prior Publication Data

US 2022/0338876 A1  Oct. 27, 2022

Related U.S. Application Data

(63) Continuation of application No. 16/739,336, filed on Jan. 10, 2020, now Pat. No. 11,376,006.

(Continued)

(51) Int. Cl.
*A61B 17/115* (2006.01)
*H05K 1/02* (2006.01)
(Continued)

(52) U.S. Cl.
CPC ........ *A61B 17/1155* (2013.01); *H05K 1/0277* (2013.01); *H05K 7/1427* (2013.01);
(Continued)

(58) Field of Classification Search
CPC . A61B 17/1155; H05K 7/1427; H05K 1/0277
See application file for complete search history.

(56) References Cited

U.S. PATENT DOCUMENTS

| 37,165 A | 12/1862 | Gary |
| 3,209,754 A | 10/1965 | Brown |

(Continued)

FOREIGN PATENT DOCUMENTS

| CN | 101683284 A | 3/2010 |
| CN | 102648864 A | 8/2012 |

(Continued)

OTHER PUBLICATIONS

U.S. Appl. No. 16/808,561, filed 2020.

(Continued)

*Primary Examiner* — Nathaniel C Chukwurah
(74) *Attorney, Agent, or Firm* — Carter, DeLuca & Farrell LLP

(57) ABSTRACT

A surgical device includes a handle assembly having a controller and an adapter assembly including a tubular housing having a proximal end portion configured to couple to the handle assembly and a distal end portion. The adapter assembly also includes a load sensing assembly disposed with the tubular housing. The load sensing assembly is configured to measure a load exerted on the tubular housing and includes: a sensor body having a pocket defined therein; a load sensor circuit disposed within the pocket and coupled to the sensor body; and a signal processing circuit disposed within the pocket and electrically coupled to the load sensor circuit. The load sensing assembly further includes a cover disposed over the pocket and enclosing the load sensor circuit and the signal processing circuit therein, the cover being coupled to the sensor body thereby forming a first hermetic seal therebetween. The surgical device further (Continued)

includes a surgical end effector configured to couple to the distal end portion of the adapter assembly.

21 Claims, 14 Drawing Sheets

Related U.S. Application Data

(60) Provisional application No. 62/801,979, filed on Feb. 6, 2019.

(51) Int. Cl.
*H05K 7/14* (2006.01)
*A61B 17/00* (2006.01)
*A61B 17/072* (2006.01)
*A61B 17/295* (2006.01)
*A61B 90/00* (2016.01)

(52) U.S. Cl.
CPC ............... *A61B 2017/00022* (2013.01); *A61B 2017/00486* (2013.01); *A61B 2017/07257* (2013.01); *A61B 2017/07271* (2013.01); *A61B 2017/07285* (2013.01); *A61B 17/295* (2013.01); *A61B 2090/064* (2016.02); *A61B 2562/0252* (2013.01); *A61B 2562/164* (2013.01); *A61B 2562/166* (2013.01)

(56) References Cited

U.S. PATENT DOCUMENTS

| | | |
|---|---|---|
| 3,273,562 A | 9/1966 | Brown |
| 3,499,591 A | 3/1970 | Green |
| 3,528,693 A | 9/1970 | Pearson et al. |
| 3,744,495 A | 7/1973 | Johnson |
| 3,862,631 A | 1/1975 | Austin |
| 3,949,924 A | 4/1976 | Green |
| 4,060,089 A | 11/1977 | Noiles |
| 4,204,623 A | 5/1980 | Green |
| 4,217,902 A | 8/1980 | March |
| 4,263,903 A | 4/1981 | Griggs |
| 4,275,813 A | 6/1981 | Noiles |
| 4,331,277 A | 5/1982 | Green |
| 4,428,376 A | 1/1984 | Mericle |
| 4,429,695 A | 2/1984 | Green |
| 4,444,181 A | 4/1984 | Wevers et al. |
| 4,454,875 A | 6/1984 | Pratt et al. |
| 4,456,006 A | 6/1984 | Wevers et al. |
| 4,485,816 A | 12/1984 | Krumme |
| 4,485,817 A | 12/1984 | Swiggett |
| 4,488,523 A | 12/1984 | Shichman |
| 4,508,253 A | 4/1985 | Green |
| 4,508,523 A | 4/1985 | Leu |
| 4,522,206 A | 6/1985 | Whipple et al. |
| 4,534,350 A | 8/1985 | Golden et al. |
| 4,535,772 A | 8/1985 | Sheehan |
| 4,566,620 A | 1/1986 | Green et al. |
| 4,570,623 A | 2/1986 | Ellison et al. |
| 4,606,343 A | 8/1986 | Conta et al. |
| 4,606,344 A | 8/1986 | Di Giovanni |
| 4,610,383 A | 9/1986 | Rothfuss et al. |
| 4,612,923 A | 9/1986 | Kronenthal |
| 4,612,933 A | 9/1986 | Brinkerhoff et al. |
| D286,442 S | 10/1986 | Korthoff et al. |
| 4,627,437 A | 12/1986 | Bedi et al. |
| 4,635,637 A | 1/1987 | Schreiber |
| 4,662,371 A | 5/1987 | Whipple et al. |
| 4,671,280 A | 6/1987 | Dorband et al. |
| 4,705,038 A | 11/1987 | Sjostrom et al. |
| 4,712,550 A | 12/1987 | Sinnett |
| 4,719,917 A | 1/1988 | Barrows et al. |
| 4,724,839 A | 2/1988 | Bedi et al. |
| 4,731,058 A | 3/1988 | Doan |
| 4,805,617 A | 2/1989 | Bedi et al. |
| 4,807,628 A | 2/1989 | Peters et al. |
| 4,852,558 A | 8/1989 | Outerbridge |
| 4,913,144 A | 4/1990 | Del Medico |
| 4,960,420 A | 10/1990 | Goble et al. |
| 4,962,877 A | 10/1990 | Hervas |
| 4,990,153 A | 2/1991 | Richards |
| 4,994,073 A | 2/1991 | Green |
| 4,995,877 A | 2/1991 | Ams et al. |
| 5,040,715 A | 8/1991 | Green et al. |
| 5,065,929 A | 11/1991 | Schulze et al. |
| 5,089,009 A | 2/1992 | Green |
| 5,108,422 A | 4/1992 | Green et al. |
| 5,114,399 A | 5/1992 | Kovalcheck |
| 5,129,570 A | 7/1992 | Schulze et al. |
| 5,143,453 A | 9/1992 | Weynant nee Girones |
| 5,203,864 A | 4/1993 | Phillips |
| 5,207,697 A | 5/1993 | Carusillo et al. |
| 5,209,756 A | 5/1993 | Seedhom et al. |
| 5,246,443 A | 9/1993 | Mai |
| 5,258,008 A | 11/1993 | Wilk |
| 5,271,543 A | 12/1993 | Grant et al. |
| RE34,519 E | 1/1994 | Fox et al. |
| 5,282,829 A | 2/1994 | Hermes |
| 5,300,081 A | 4/1994 | Young et al. |
| 5,307,976 A | 5/1994 | Olson et al. |
| 5,312,023 A | 5/1994 | Green et al. |
| 5,312,024 A | 5/1994 | Grant et al. |
| 5,313,935 A | 5/1994 | Kortenbach et al. |
| 5,318,221 A | 6/1994 | Green et al. |
| 5,326,013 A | 7/1994 | Green et al. |
| 5,330,486 A | 7/1994 | Wilk |
| 5,332,142 A | 7/1994 | Robinson et al. |
| 5,342,376 A | 8/1994 | Ruff |
| 5,350,355 A | 9/1994 | Sklar |
| 5,356,064 A | 10/1994 | Green et al. |
| 5,359,993 A | 11/1994 | Slater et al. |
| 5,364,001 A | 11/1994 | Bryan |
| 5,381,943 A | 1/1995 | Allen et al. |
| 5,383,874 A | 1/1995 | Jackson et al. |
| 5,383,880 A | 1/1995 | Hooven |
| 5,389,098 A | 2/1995 | Tsuruta et al. |
| 5,391,166 A | 2/1995 | Eggers |
| 5,395,030 A | 3/1995 | Kuramoto et al. |
| 5,395,033 A | 3/1995 | Byrne et al. |
| 5,400,267 A | 3/1995 | Denen et al. |
| 5,403,312 A | 4/1995 | Yates et al. |
| 5,405,344 A | 4/1995 | Williamson et al. |
| 5,411,508 A | 5/1995 | Bessler et al. |
| 5,413,267 A | 5/1995 | Solyntjes et al. |
| 5,431,323 A | 7/1995 | Smith et al. |
| 5,464,144 A | 11/1995 | Guy et al. |
| 5,467,911 A | 11/1995 | Tsuruta et al. |
| 5,478,344 A | 12/1995 | Stone et al. |
| 5,482,100 A | 1/1996 | Kuhar |
| 5,485,947 A | 1/1996 | Olson et al. |
| 5,487,499 A | 1/1996 | Sorrentino et al. |
| 5,490,427 A | 2/1996 | Yee |
| 5,497,933 A | 3/1996 | DeFonzo et al. |
| 5,500,000 A | 3/1996 | Feagin et al. |
| 5,503,320 A | 4/1996 | Webster et al. |
| 5,507,743 A | 4/1996 | Edwards et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,531,744 A | 7/1996 | Nardella et al. |
| 5,533,661 A | 7/1996 | Main et al. |
| 5,535,934 A | 7/1996 | Boiarski et al. |
| 5,535,937 A | 7/1996 | Boiarski et al. |
| 5,558,671 A | 9/1996 | Yates |
| 5,560,532 A | 10/1996 | DeFonzo et al. |
| 5,562,239 A | 10/1996 | Boiarski et al. |
| 5,571,285 A | 11/1996 | Chow et al. |
| 5,575,799 A | 11/1996 | Bolanos et al. |
| 5,582,611 A | 12/1996 | Tsuruta et al. |
| 5,584,835 A | 12/1996 | Greenfield |
| 5,601,224 A | 2/1997 | Bishop et al. |
| 5,601,558 A | 2/1997 | Torrie et al. |
| 5,607,095 A | 3/1997 | Smith et al. |

(56) References Cited

U.S. PATENT DOCUMENTS

| | | |
|---|---|---|
| 5,609,285 A | 3/1997 | Grant et al. |
| 5,609,560 A | 3/1997 | Ichikawa et al. |
| 5,624,452 A | 4/1997 | Yates |
| 5,632,433 A | 5/1997 | Grant et al. |
| 5,634,926 A | 6/1997 | Jobe |
| 5,642,848 A | 7/1997 | Ludwig et al. |
| 5,653,374 A | 8/1997 | Young et al. |
| 5,658,300 A | 8/1997 | Bito et al. |
| 5,658,312 A | 8/1997 | Green et al. |
| 5,662,662 A | 9/1997 | Bishop et al. |
| 5,665,085 A | 9/1997 | Nardella |
| 5,667,513 A | 9/1997 | Torrie et al. |
| 5,667,517 A | 9/1997 | Hooven |
| 5,667,527 A | 9/1997 | Cook |
| 5,669,544 A | 9/1997 | Schulze et al. |
| 5,673,841 A | 10/1997 | Schulze et al. |
| 5,676,674 A | 10/1997 | Bolanos et al. |
| 5,680,981 A | 10/1997 | Mililli et al. |
| 5,680,982 A | 10/1997 | Schulze et al. |
| 5,690,675 A | 11/1997 | Sawyer et al. |
| 5,692,668 A | 12/1997 | Schulze et al. |
| 5,695,506 A | 12/1997 | Pike et al. |
| 5,695,524 A | 12/1997 | Kelley et al. |
| 5,702,447 A | 12/1997 | Walch et al. |
| 5,704,534 A | 1/1998 | Huitema et al. |
| 5,713,505 A | 2/1998 | Huitema |
| 5,713,896 A | 2/1998 | Nardella |
| 5,715,987 A | 2/1998 | Kelley et al. |
| 5,716,366 A | 2/1998 | Yates |
| 5,720,753 A | 2/1998 | Sander et al. |
| 5,725,529 A | 3/1998 | Nicholson et al. |
| 5,728,110 A | 3/1998 | Vidal et al. |
| 5,728,116 A | 3/1998 | Rosenman |
| 5,730,757 A | 3/1998 | Benetti et al. |
| 5,735,848 A | 4/1998 | Yates et al. |
| 5,738,474 A | 4/1998 | Blewett |
| 5,755,726 A | 5/1998 | Pratt et al. |
| 5,759,171 A | 6/1998 | Coelho et al. |
| 5,779,130 A | 7/1998 | Alesi et al. |
| 5,782,397 A | 7/1998 | Koukline |
| 5,785,713 A | 7/1998 | Jobe |
| 5,788,698 A | 8/1998 | Savornin |
| 5,810,811 A | 9/1998 | Yates et al. |
| 5,823,066 A | 10/1998 | Huitema et al. |
| 5,829,662 A | 11/1998 | Allen et al. |
| 5,830,121 A | 11/1998 | Enomoto et al. |
| 5,849,023 A | 12/1998 | Mericle |
| 5,849,028 A | 12/1998 | Chen |
| 5,855,311 A | 1/1999 | Hamblin et al. |
| 5,861,005 A | 1/1999 | Kontos |
| 5,865,361 A | 2/1999 | Milliman et al. |
| 5,876,401 A | 3/1999 | Schulze et al. |
| 5,891,156 A | 4/1999 | Gessner et al. |
| 5,893,813 A | 4/1999 | Yamamoto |
| 5,895,396 A | 4/1999 | Day et al. |
| 5,906,607 A | 5/1999 | Taylor et al. |
| 5,911,721 A | 6/1999 | Nicholson et al. |
| 5,918,791 A | 7/1999 | Sorrentino et al. |
| 5,928,222 A | 7/1999 | Kleinerman |
| 5,944,717 A | 8/1999 | Lee et al. |
| 5,944,736 A | 8/1999 | Taylor et al. |
| 5,954,259 A | 9/1999 | Viola et al. |
| 5,961,521 A | 10/1999 | Roger |
| 5,964,394 A | 10/1999 | Robertson |
| 5,968,044 A | 10/1999 | Nicholson et al. |
| 5,976,171 A | 11/1999 | Taylor |
| 5,980,518 A | 11/1999 | Carr et al. |
| 5,980,548 A | 11/1999 | Evans et al. |
| 5,991,355 A | 11/1999 | Dahlke |
| 5,991,650 A | 11/1999 | Swanson et al. |
| 5,992,724 A | 11/1999 | Snyder |
| 5,997,552 A | 12/1999 | Person et al. |
| 6,004,335 A | 12/1999 | Vaitekunas et al. |
| 6,007,550 A | 12/1999 | Wang et al. |
| 6,010,054 A | 1/2000 | Johnson et al. |
| 6,013,077 A | 1/2000 | Harwin |
| 6,015,417 A | 1/2000 | Reynolds, Jr. |
| 6,017,354 A | 1/2000 | Culp et al. |
| 6,030,410 A | 2/2000 | Zurbrugg |
| 6,032,849 A | 3/2000 | Mastri et al. |
| 6,039,731 A | 3/2000 | Taylor et al. |
| 6,051,007 A | 4/2000 | Hogendijk et al. |
| 6,063,078 A | 5/2000 | Wittkampf |
| 6,063,095 A | 5/2000 | Wang et al. |
| 6,077,246 A | 6/2000 | Kullas et al. |
| 6,079,606 A | 6/2000 | Milliman et al. |
| 6,080,150 A | 6/2000 | Gough |
| 6,083,242 A | 7/2000 | Cook |
| 6,090,123 A | 7/2000 | Culp et al. |
| 6,092,422 A | 7/2000 | Binnig et al. |
| 6,109,500 A | 8/2000 | Alli et al. |
| 6,113,592 A | 9/2000 | Taylor |
| 6,123,702 A | 9/2000 | Swanson et al. |
| H1904 H | 10/2000 | Yates et al. |
| 6,126,058 A | 10/2000 | Adams et al. |
| 6,126,651 A | 10/2000 | Mayer |
| 6,127,811 A | 10/2000 | Shenoy et al. |
| 6,132,425 A | 10/2000 | Gough |
| 6,165,169 A | 12/2000 | Panescu et al. |
| 6,166,538 A | 12/2000 | D'Alfonso |
| 6,179,840 B1 | 1/2001 | Bowman |
| 6,187,009 B1 | 2/2001 | Herzog et al. |
| 6,187,019 B1 | 2/2001 | Stefanchik et al. |
| 6,190,401 B1 | 2/2001 | Green et al. |
| 6,193,501 B1 | 2/2001 | Masel et al. |
| 6,202,914 B1 | 3/2001 | Geiste et al. |
| 6,217,573 B1 | 4/2001 | Webster |
| 6,228,534 B1 | 5/2001 | Takeuchi et al. |
| 6,231,565 B1 | 5/2001 | Tovey et al. |
| 6,236,874 B1 | 5/2001 | Devlin et al. |
| 6,237,604 B1 | 5/2001 | Burnside et al. |
| 6,241,139 B1 | 6/2001 | Milliman et al. |
| 6,245,065 B1 | 6/2001 | Panescu et al. |
| 6,248,117 B1 | 6/2001 | Blatter |
| 6,250,532 B1 | 6/2001 | Green et al. |
| 6,258,111 B1 | 7/2001 | Ross et al. |
| 6,264,086 B1 | 7/2001 | McGuckin, Jr. |
| 6,264,087 B1 | 7/2001 | Whitman |
| 6,264,653 B1 | 7/2001 | Falwell |
| 6,281,471 B1 | 8/2001 | Smart |
| 6,288,534 B1 | 9/2001 | Starkweather et al. |
| 6,290,701 B1 | 9/2001 | Enayati |
| 6,293,943 B1 | 9/2001 | Panescu et al. |
| 6,295,330 B1 | 9/2001 | Skog et al. |
| 6,315,184 B1 | 11/2001 | Whitman |
| 6,329,778 B1 | 12/2001 | Culp et al. |
| 6,330,965 B1 | 12/2001 | Milliman et al. |
| 6,346,104 B2 | 2/2002 | Daly et al. |
| 6,355,066 B1 | 3/2002 | Kim |
| 6,364,884 B1 | 4/2002 | Bowman et al. |
| 6,387,092 B1 | 5/2002 | Burnside et al. |
| 6,388,240 B2 | 5/2002 | Schulz et al. |
| 6,402,766 B2 | 6/2002 | Bowman et al. |
| H2037 H | 7/2002 | Yates et al. |
| 6,412,279 B1 | 7/2002 | Coleman et al. |
| 6,425,903 B1 | 7/2002 | Voegele |
| 6,436,097 B1 | 8/2002 | Nardella |
| 6,436,107 B1 | 8/2002 | Wang et al. |
| 6,436,110 B2 | 8/2002 | Bowman et al. |
| 6,443,973 B1 | 9/2002 | Whitman |
| 6,447,517 B1 | 9/2002 | Bowman |
| 6,461,372 B1 | 10/2002 | Jensen et al. |
| 6,478,210 B2 | 11/2002 | Adams et al. |
| 6,497,707 B1 | 12/2002 | Bowman et al. |
| 6,505,768 B2 | 1/2003 | Whitman |
| 6,515,273 B2 | 2/2003 | Al-Ali |
| 6,524,316 B1 | 2/2003 | Nicholson et al. |
| 6,533,157 B1 | 3/2003 | Whitman |
| 6,540,751 B2 | 4/2003 | Enayati |
| 6,544,273 B1 | 4/2003 | Harari et al. |
| 6,554,852 B1 | 4/2003 | Oberlander |
| 6,562,071 B2 | 5/2003 | Jarvinen |
| 6,578,579 B2 | 6/2003 | Burnside et al. |
| 6,601,748 B1 | 8/2003 | Fung et al. |

(56) References Cited

U.S. PATENT DOCUMENTS

| | | |
|---|---|---|
| 6,601,749 B2 | 8/2003 | Sullivan et al. |
| 6,602,252 B2 | 8/2003 | Mollenauer |
| 6,611,793 B1 | 8/2003 | Burnside et al. |
| 6,616,821 B2 | 9/2003 | Broadley et al. |
| 6,629,986 B1 | 10/2003 | Ross et al. |
| 6,651,669 B1 | 11/2003 | Burnside |
| 6,656,177 B2 | 12/2003 | Truckai et al. |
| 6,669,073 B2 | 12/2003 | Milliman et al. |
| 6,669,705 B2 | 12/2003 | Westhaver et al. |
| 6,696,008 B2 | 2/2004 | Brandinger |
| 6,698,643 B2 | 3/2004 | Whitman |
| 6,699,177 B1 | 3/2004 | Wang et al. |
| 6,716,233 B1 | 4/2004 | Whitman |
| 6,736,085 B1 | 5/2004 | Esnouf |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,843,403 B2 | 1/2005 | Whitman |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,861,639 B2 | 3/2005 | Al-Ali |
| 6,872,214 B2 | 3/2005 | Sonnenschein et al. |
| 6,899,538 B2 | 5/2005 | Matoba |
| 6,900,004 B2 | 5/2005 | Satake |
| 6,905,057 B2 | 6/2005 | Swayze et al. |
| 6,926,636 B2 | 8/2005 | Luper |
| 6,953,139 B2 | 10/2005 | Milliman et al. |
| 6,959,852 B2 | 11/2005 | Shelton, IV et al. |
| 6,964,363 B2 | 11/2005 | Wales et al. |
| 6,979,328 B2 | 12/2005 | Baerveldt et al. |
| 6,981,628 B2 | 1/2006 | Wales |
| 6,981,941 B2 | 1/2006 | Whitman et al. |
| 6,988,649 B2 | 1/2006 | Shelton, IV et al. |
| 7,000,819 B2 | 2/2006 | Swayze et al. |
| 7,032,798 B2 | 4/2006 | Whitman et al. |
| 7,044,353 B2 | 5/2006 | Mastri et al. |
| 7,048,687 B1 | 5/2006 | Reuss et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,083,075 B2 | 8/2006 | Swayze et al. |
| 7,097,089 B2 | 8/2006 | Marczyk |
| 7,111,769 B2 | 9/2006 | Wales et al. |
| 7,118,564 B2 | 10/2006 | Ritchie et al. |
| 7,122,029 B2 | 10/2006 | Koop et al. |
| 7,128,253 B2 | 10/2006 | Mastri et al. |
| 7,128,254 B2 | 10/2006 | Shelton, IV et al. |
| 7,140,528 B2 | 11/2006 | Shelton, IV |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,186,966 B2 | 3/2007 | Al-Ali |
| 7,193,519 B2 | 3/2007 | Root et al. |
| 7,217,269 B2 | 5/2007 | El-Galley et al. |
| 7,220,232 B2 | 5/2007 | Suorsa et al. |
| 7,240,817 B2 | 7/2007 | Higuchi |
| 7,241,270 B2 | 7/2007 | Horzewski et al. |
| 7,246,734 B2 | 7/2007 | Shelton, IV |
| 7,303,108 B2 | 12/2007 | Shelton, IV |
| 7,328,828 B2 | 2/2008 | Ortiz et al. |
| 7,335,169 B2 | 2/2008 | Thompson et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,416,101 B2 | 8/2008 | Shelton, IV et al. |
| 7,419,080 B2 | 9/2008 | Smith et al. |
| 7,422,136 B1 | 9/2008 | Marczyk |
| 7,422,139 B2 | 9/2008 | Shelton, IV et al. |
| 7,431,188 B1 | 10/2008 | Marczyk |
| 7,431,189 B2 | 10/2008 | Shelton, IV et al. |
| 7,434,715 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,461,767 B2 | 12/2008 | Viola et al. |
| 7,464,600 B2 | 12/2008 | Kurtz |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,348 B2 | 1/2009 | Marczyk |
| 7,487,899 B2 | 2/2009 | Shelton, IV et al. |
| 7,549,563 B2 | 6/2009 | Mather et al. |
| 7,552,854 B2 | 6/2009 | Wixey et al. |
| 7,556,185 B2 | 7/2009 | Viola |
| 7,568,603 B2 | 8/2009 | Shelton, IV et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,648,055 B2 | 1/2010 | Marczyk |
| 7,670,334 B2 | 3/2010 | Hueil et al. |
| 7,694,809 B2 | 4/2010 | Garbini et al. |
| 7,721,931 B2 | 5/2010 | Shelton, IV et al. |
| 7,740,159 B2 | 6/2010 | Shelton, IV et al. |
| 7,753,248 B2 | 7/2010 | Viola |
| 7,757,925 B2 | 7/2010 | Viola et al. |
| 7,766,207 B2 | 8/2010 | Mather et al. |
| 7,766,210 B2 | 8/2010 | Shelton, IV et al. |
| 7,770,775 B2 | 8/2010 | Shelton, IV et al. |
| 7,784,663 B2 | 8/2010 | Shelton, IV |
| 7,815,090 B2 | 10/2010 | Marczyk |
| 7,823,760 B2 | 11/2010 | Zemlok et al. |
| 7,845,534 B2 | 12/2010 | Viola et al. |
| 7,870,989 B2 | 1/2011 | Viola et al. |
| 7,886,953 B2 | 2/2011 | Schwemberger et al. |
| 7,887,530 B2 | 2/2011 | Zemlok et al. |
| 7,905,897 B2 | 3/2011 | Whitman et al. |
| 7,909,221 B2 | 3/2011 | Viola et al. |
| 7,922,063 B2 | 4/2011 | Zemlok et al. |
| 7,931,660 B2 | 4/2011 | Aranyi et al. |
| 7,950,560 B2 | 5/2011 | Zemlok et al. |
| 7,955,352 B2 | 6/2011 | McEwen et al. |
| 8,006,885 B2 | 8/2011 | Marczyk |
| 8,006,887 B2 | 8/2011 | Marczyk |
| 8,011,551 B2 | 9/2011 | Marczyk et al. |
| 8,020,742 B2 | 9/2011 | Marczyk |
| 8,025,199 B2 | 9/2011 | Whitman et al. |
| 8,038,044 B2 | 10/2011 | Viola |
| 8,052,024 B2 | 11/2011 | Viola et al. |
| 8,066,721 B2 | 11/2011 | Kortenbach et al. |
| 8,074,858 B2 | 12/2011 | Marczyk |
| 8,092,493 B2 | 1/2012 | Marczyk |
| 8,128,645 B2 | 3/2012 | Sonnenschein et al. |
| 8,132,705 B2 | 3/2012 | Viola et al. |
| 8,157,150 B2 | 4/2012 | Viola et al. |
| 8,186,555 B2 | 5/2012 | Shelton, IV et al. |
| 8,201,721 B2 | 6/2012 | Zemlok et al. |
| 8,210,412 B2 | 7/2012 | Marczyk |
| 8,240,536 B2 | 8/2012 | Marczyk |
| 8,240,537 B2 | 8/2012 | Marczyk |
| 8,267,924 B2 | 9/2012 | Zemlok et al. |
| 8,328,823 B2 | 12/2012 | Aranyi et al. |
| 8,348,125 B2 | 1/2013 | Viola et al. |
| 11,376,006 B2 * | 7/2022 | Sgroi, Jr. ............ H05K 7/1427 |
| 2002/0103489 A1 | 8/2002 | Ku |
| 2002/0111641 A1 | 8/2002 | Peterson et al. |
| 2002/0165541 A1 | 11/2002 | Whitman |
| 2003/0090201 A1 | 5/2003 | Peng |
| 2003/0114851 A1 | 6/2003 | Truckai et al. |
| 2003/0120306 A1 | 6/2003 | Burbank et al. |
| 2004/0232201 A1 | 11/2004 | Wenchell et al. |
| 2005/0006429 A1 | 1/2005 | Wales et al. |
| 2005/0010235 A1 | 1/2005 | VanDusseldorp |
| 2005/0131390 A1 | 6/2005 | Heinrich et al. |
| 2005/0139636 A1 | 6/2005 | Schwemberger et al. |
| 2005/0177176 A1 | 8/2005 | Gerbi et al. |
| 2005/0192609 A1 | 9/2005 | Whitman et al. |
| 2005/0247753 A1 | 11/2005 | Kelly et al. |
| 2006/0000867 A1 | 1/2006 | Shelton et al. |
| 2007/0023477 A1 | 2/2007 | Whitman et al. |
| 2007/0029363 A1 | 2/2007 | Popov |

(56) References Cited

U.S. PATENT DOCUMENTS

| | | |
|---|---|---|
| 2007/0084897 A1 | 4/2007 | Shelton et al. |
| 2007/0102472 A1 | 5/2007 | Shelton |
| 2007/0175949 A1 | 8/2007 | Shelton et al. |
| 2007/0175950 A1 | 8/2007 | Shelton, IV et al. |
| 2007/0175951 A1 | 8/2007 | Shelton et al. |
| 2007/0175955 A1 | 8/2007 | Shelton et al. |
| 2007/0219563 A1 | 9/2007 | Voegele |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0135600 A1 | 6/2008 | Hiranuma |
| 2008/0169329 A1 | 7/2008 | Shelton et al. |
| 2008/0185419 A1 | 8/2008 | Smith et al. |
| 2008/0197167 A1 | 8/2008 | Viola et al. |
| 2008/0255413 A1 | 10/2008 | Zemlok et al. |
| 2008/0255607 A1 | 10/2008 | Zemlok |
| 2009/0018624 A1 | 1/2009 | Levinson et al. |
| 2009/0090201 A1 | 4/2009 | Viola |
| 2009/0090763 A1 | 4/2009 | Zemlok et al. |
| 2010/0200636 A1 | 8/2010 | Zemlok et al. |
| 2010/0312257 A1 | 12/2010 | Aranyi |
| 2010/0320254 A1 | 12/2010 | Zemlok et al. |
| 2011/0034910 A1 | 2/2011 | Ross et al. |
| 2011/0062211 A1 | 3/2011 | Ross et al. |
| 2011/0168757 A1 | 7/2011 | Viola et al. |
| 2011/0172681 A1 | 7/2011 | Aranyi et al. |
| 2011/0190738 A1 | 8/2011 | Zemlok et al. |
| 2011/0301579 A1 | 12/2011 | Marczyk et al. |
| 2011/0303735 A1 | 12/2011 | Marczyk |
| 2012/0055972 A1 | 3/2012 | Marczyk |
| 2012/0074197 A1 | 3/2012 | Marczyk |
| 2012/0175400 A1 | 7/2012 | Viola et al. |
| 2012/0193393 A1 | 8/2012 | Viola et al. |
| 2012/0198288 A1 | 8/2012 | Njo et al. |
| 2012/0220989 A1 | 8/2012 | Zemlok et al. |
| 2012/0223121 A1 | 9/2012 | Viola et al. |
| 2012/0241494 A1 | 9/2012 | Marczyk |
| 2012/0277790 A1 | 11/2012 | Zemlok et al. |
| 2012/0298718 A1 | 11/2012 | Marczyk |
| 2012/0298720 A1 | 11/2012 | Marczyk |
| 2014/0190275 A1* | 7/2014 | McILravey ........... G01L 5/1627 73/862.29 |
| 2018/0042610 A1 | 2/2018 | Sgroi, Jr. |

FOREIGN PATENT DOCUMENTS

| | | |
|---|---|---|
| EP | 0537570 A2 | 4/1993 |
| EP | 0647431 A2 | 4/1995 |
| EP | 0738501 A1 | 10/1996 |
| EP | 0770354 A1 | 5/1997 |
| EP | 1070487 A2 | 1/2001 |
| EP | 1201196 A1 | 5/2002 |
| EP | 1658817 A1 | 5/2006 |
| EP | 1813203 A2 | 8/2007 |
| EP | 2696163 A1 | 2/2014 |
| EP | 3284416 A1 | 2/2018 |
| EP | 3293503 A1 | 3/2018 |
| EP | 3366229 A1 | 8/2018 |
| FR | 2849589 A1 | 7/2004 |
| JP | 3252539 B2 | 2/2002 |
| JP | 6421329 B2 | 11/2018 |
| WO | 94/14129 A1 | 6/1994 |
| WO | 9729694 A1 | 8/1997 |
| WO | 9740760 A1 | 11/1997 |
| WO | 9837825 A1 | 9/1998 |
| WO | 9952489 A1 | 10/1999 |
| WO | 0234140 A2 | 5/2002 |
| WO | 03026511 A1 | 4/2003 |
| WO | 03030743 A2 | 4/2003 |
| WO | 2004032760 A2 | 4/2004 |
| WO | 2006113394 A2 | 10/2006 |
| WO | 2007014355 A2 | 2/2007 |
| WO | 2007030753 A2 | 3/2007 |
| WO | 2007114868 A2 | 10/2007 |
| WO | 2007118179 A2 | 10/2007 |
| WO | 2009143092 A1 | 11/2009 |
| WO | 2015095933 A1 | 7/2015 |

OTHER PUBLICATIONS

Extended European Search Report issued in corresponding European Appl. No. 20155571.1 dated Jun. 24, 2020 (8 pages).

Detemple, P., "Microtechnology in Modem Health Care", Med Device Technol. 9(9):18-25 (1998).

Abridged Data Sheet, "DeepCover Secure Authenticator with 1-Wire SHA-256 and 512-Bit User EEPROM", Maxim Integrated Products, Inc. pp. 1-4; 42; Dec. 2012.

Data Sheet "DS28E15-1-Sire SHA-256 Secure Authenticator with 512-Bit User EEPROM"; IC-On-line, Electronic Component Manufacturers, pp. 1-2; Aug. 2013.

European Examination Report issued in corresponding application EP 20155571.1 dated Jul. 18, 2023 (5 pages).

Chinese Office Action issued in corresponding application No. 202010079683.X, dated Dec. 2, 2023, together with English language translation (19 pages).

Japanese Office Action issued in corresponding application No. JP 2020-13265 dated Jan. 23, 2024, together with English language translation (8 pages).

* cited by examiner

END EFFECTOR FORCE MEASUREMENT WITH DIGITAL DRIVE CIRCUIT

CROSS-REFERENCE TO RELATED APPLICATIONS

This application is a continuation of U.S. patent application Ser. No. 16/739,336, filed Jan. 10, 2020, now U.S. Pat. No. 11,376,006, which claims the benefit of and priority to U.S. Provisional Patent Application Ser. No. 62/801,979 filed Feb. 6, 2019. The entire disclosures of each of the foregoing applications are incorporated by reference herein.

BACKGROUND

1. Technical Field

The present disclosure relates to surgical devices. More specifically, the present disclosure relates to handheld electromechanical surgical systems for performing surgical procedures having reusable components with load sensing devices.

2. Background of Related Art

One type of surgical device is a circular clamping, cutting and stapling device. Such a device may be employed in a surgical procedure to reattach rectum portions that were previously transected, or similar procedures. Conventional circular clamping, cutting, and stapling devices include a pistol or linear grip-styled structure having an elongated shaft extending therefrom and a staple cartridge supported on the distal end of the elongated shaft. In this instance, a physician may insert the loading unit portion of the circular stapling device into a rectum of a patient and maneuver the device up the colonic tract of the patient toward the transected rectum portions. The loading unit includes a cartridge assembly having a plurality of staples. Along the proximal portion of the transected colon, an anvil assembly can be purse stringed therein. Alternatively, if desired, the anvil portion can be inserted into the colon through an incision proximal to the transected colon. The anvil and cartridge assemblies are approximated toward one another and staples are ejected from the cartridge assembly toward the anvil assembly thereby forming the staples in tissue to affect an end-to-end anastomosis, and an annular knife is fired to core a portion of the clamped tissue portions. After the end-to-end anastomosis has been effected, the circular stapling device is removed from the surgical site.

A number of surgical device manufacturers have also developed proprietary powered drive systems for operating and/or manipulating the end effectors. The powered drive systems may include a powered handle assembly, which may be reusable, and a disposable end effector that is removably connected to the powered handle assembly.

Many of the existing end effectors for use with existing powered surgical devices and/or handle assemblies are driven by a linear driving force. For example, end effectors for performing endo-gastrointestinal anastomosis procedures, end-to-end anastomosis procedures and transverse anastomosis procedures, are actuated by a linear driving force. As such, these end effectors are not compatible with surgical devices and/or handle assemblies that use rotary motion.

In order to make the linear driven end effectors compatible with powered surgical devices that use a rotary motion to deliver power, a need exists for adapters to interconnect the linear driven end effectors with the powered rotary driven surgical devices. These adapters may also be reusable, and as such, need to able to withstand multiple sterilization cycles.

As these adapters are becoming more sophisticated and include various electronic components, there is a need for electronic components disposed within the adapters that can withstand multiple autoclave cycles.

SUMMARY

Powered surgical devices may include various sensors for providing feedback during their operation. However, one limitation of the electronics and sensors used in the sterile environment of the operating room is that they need to be designed to withstand multiple cleaning and autoclave cycles. In order to gather information of the mechanical forces applied by the powered surgical devices, load sensing devices, such as load cells, are disposed on one or more mechanical components of the powered surgical device and/or adapters coupled thereto.

Load sensing devices are also coupled to signal processing and conditioning circuits that are separately packaged from the load sensing devices. In particular, components of signal processing circuits are usually disposed on printed circuit boards ("PCB") housed with other electronic and electric components of powered surgical devices. Remote placements of these circuit components away from the load sensing devices is due to their size and shape, which prevent the PCB from being in close proximity to the load sensing devices. Accordingly, these circuits are connected to the load sensing devices through wired connections, which involve longer leads (e.g., flexible printed circuit traces over 10 centimeters) for transmitting analog signals from the load sensing devices to the signal processing circuit. Longer wired connections can result in signal loss and also increase the chances of failure due to exposure of these leads to disinfecting and sterilization cycles. Harsh environments from disinfecting solutions and residual moisture from the autoclaving processes breaks down the components and coatings in flex circuits, thereby causing signal degradation. Further, in surgical devices where saline irrigation is utilized, the saline can further breakdown of mechanical integrity of these circuits resulting in signal degradation.

In addition, the separation between the load sensing devices and the signal processing circuitry also affects fidelity of analog sense signals transmitted from the load sensing devices. The analog voltage signals are low voltage signals and are therefore more susceptible to interference of the load measured by the load sensing devices due to water ingress in the PCB, solder connections, and/or traces, small contamination including solder flux and autoclave mineral deposits, as well as radio frequency interference due to long conductor travel length. Remote placement of signal processing circuits also results in lower bit resolution. Furthermore, conventional signal processing circuits used with load sensing devices have no ability to compensate for zero balance fluctuations in load sensing devices due to inconsistencies of sensor bodies housing the load sensing devices (e.g., during manufacture and assembly of the sensors). As used herein, the term "zero balance" denotes a baseline signal from a load sensing device corresponding to a condition in which the load sensing device is unloaded.

The present disclosure provides for a combined load sensing assembly having one or more load sensing devices and a signal processing circuit disposed within a hermetically sealed housing of the sensor. This obviates the problem of transmitting analog load sensing signals along long leads and protects the load sensing devices and the signal processing circuit from exposure to elements including sterilization cycles (e.g., autoclaving). In addition, the signal processing circuit is programmable to optimize the sensor signals by adjusting gain and offset values of sensor signals.

Conventional load sensing devices that utilize strain gauge technology typically suffer from the lack of adjustability or tuning of the load sensing devices. In particular, variations in the load sensing devices, tolerances in sensor bodies, placement of the load sensing devices, and other factors, contribute to zero balance variations, which result in variable zero balance values across the lot of load sensing devices. Unfortunately, in conventional load sensing device zero balance cannot be adjusted for each individual load sensing device. The present disclosure provides a signal processing circuit that may be programmed to adjust zero balance after the load sensor is manufactures and/or assembled.

According to one embodiment of the present disclosure, a surgical device is disclosed. The surgical device includes a handle assembly having a controller and an adapter assembly including a tubular housing having a proximal end portion configured to couple to the handle assembly and a distal end portion. The adapter assembly also includes a load sensing assembly disposed with the tubular housing. The load sensing assembly is configured to measure a load exerted on the tubular housing and includes: a sensor body having a pocket defined therein; a load sensor circuit disposed within the pocket and coupled to the sensor body; and a signal processing circuit disposed within the pocket and electrically coupled to the load sensor circuit. The load sensing assembly further includes a cover disposed over the pocket and enclosing the load sensor circuit and the signal processing circuit therein, the cover being coupled to the sensor body thereby forming a first hermetic seal therebetween. The surgical device further includes a surgical end effector configured to couple to the distal end portion of the adapter assembly.

According to one aspect of the above embodiments, the handle assembly includes an electrical receptacle configured to couple to the electrical connector and the controller is coupled to the electrical receptacle.

According to another embodiment of the present disclosure, an adapter assembly is disclosed. The adapter assembly includes a tubular housing having a proximal end portion and a distal end portion and a load sensing assembly disposed with the tubular housing. The load sensing assembly is configured to measure a load exerted on the tubular housing and includes: a sensor body having a pocket defined therein; a load sensor circuit disposed within the pocket and coupled to the sensor body; and a signal processing circuit disposed within the pocket and electrically coupled to the load sensor circuit. The load sensing assembly further includes a cover disposed over the pocket and enclosing the load sensor circuit and the signal processing circuit therein, the cover being coupled to the sensor body thereby forming a first hermetic seal therebetween.

According to one aspect of any of the above embodiments, the adapter assembly further includes an actuation assembly having a trocar member. The sensor body includes a lumen defined therethrough and the trocar assembly is movable through the lumen.

According to another aspect of any of the above embodiments, the adapter assembly further includes at least one electrically conductive lead coupled to a plurality of pins of the load sensing assembly; and an electrical connector disposed at the proximal end portion and coupled to the at least one electrically conductive lead.

According to a further embodiment of the present disclosure, a load sensing assembly is disclosed. The load sensing assembly including: a sensor body having a pocket defined therein; a load sensor circuit disposed within the pocket and coupled to the sensor body; and a signal processing circuit disposed within the pocket and electrically coupled to the load sensor circuit. The load sensing assembly further includes a cover disposed over the pocket and enclosing the load sensor circuit and the signal processing circuit therein, the cover being coupled to the sensor body thereby forming a first hermetic seal therebetween.

According to one aspect of the above embodiments, the sensor body may further include a slot defined therein, the slot being connected to the pocket. The load sensing assembly may further include a header including a plurality of pins coupled to the load sensor circuit and the signal processing circuit, wherein the header is coupled to the sensor body thereby forming a second hermetic seal therebetween.

According to another aspect of the above embodiments, the load sensing assembly includes a plurality of load sensing devices.

According to a further aspect of the above embodiments, the signal processing circuit may include a flexible circuit board and may be covered by a dielectric wrap.

BRIEF DESCRIPTION OF THE DRAWINGS

Embodiments of the present disclosure are described herein with reference to the accompanying drawings, wherein.

DETAILED DESCRIPTION OF EMBODIMENTS

Figure 1:
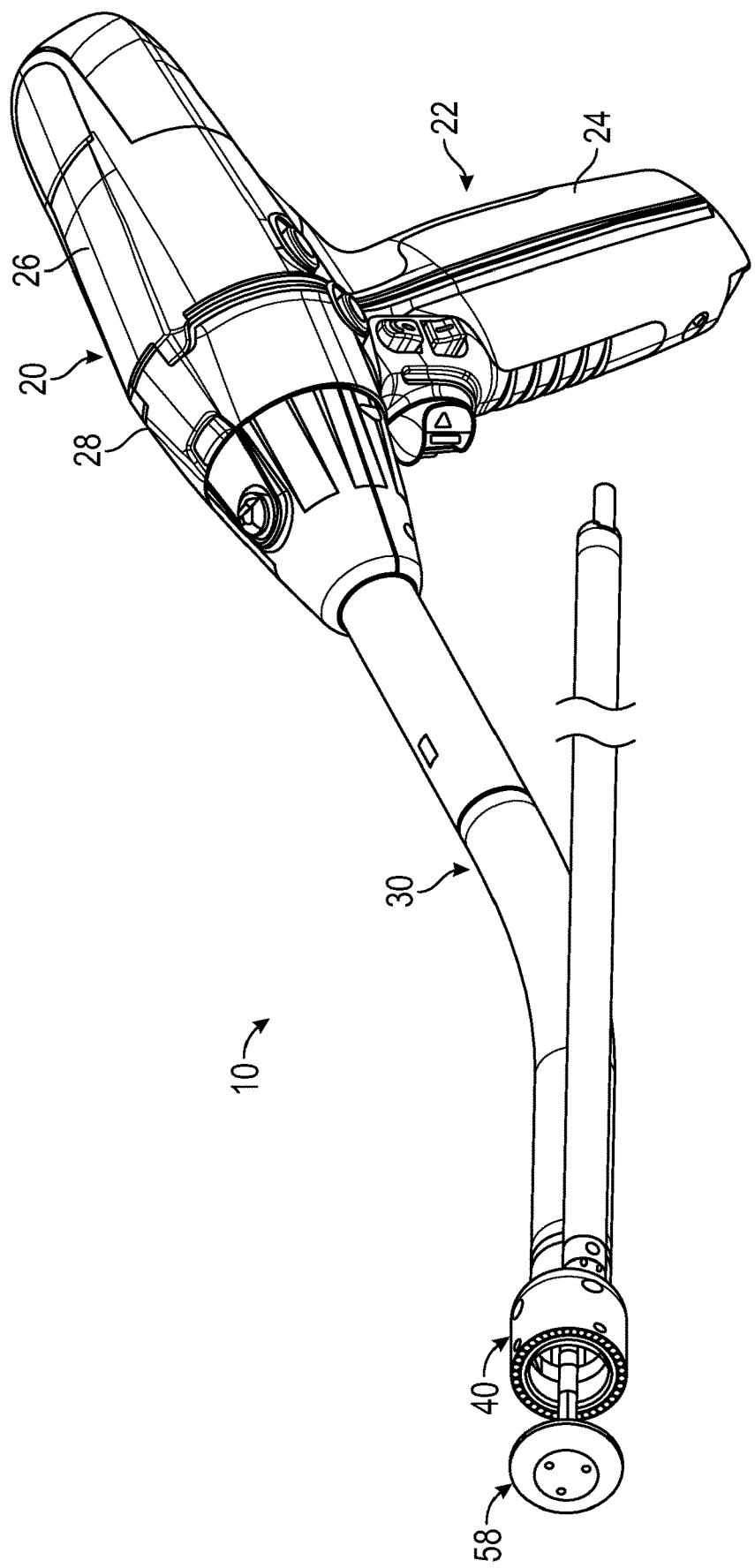
FIG. 1 is a perspective view of a handheld surgical device, an adapter assembly, an end effector having a reload and an anvil assembly according to an embodiment of the present disclosure.

Embodiments of the present disclosure are now described in detail with reference to the drawings in which like reference numerals designate identical or corresponding elements in each of the several views. As used herein, the term "clinician" refers to a doctor, a nurse or any other care provider and may include support personnel. Throughout this description, the term "proximal" will refer to the portion of the device or component thereof that is closer to the clinician and the term "distal" will refer to the portion of the device or component thereof that is farther from the clinician. Additionally, in the drawings and in the description that follows, terms such as front, rear, upper, lower, top, bottom, and similar directional terms are used simply for convenience of description and are not intended to limit the disclosure. In the following description, well-known functions or constructions are not described in detail to avoid obscuring the present disclosure in unnecessary detail.

The present disclosure relates to powered surgical devices having electronic sensors for monitoring mechanical strain and forces imparted on components of the powered surgical devices. More particularly, this disclosure relates to load measuring sensors including load sensing devices as well as analog and digital circuitry that are hermetically sealed such that the load sensors are configured to resist harsh environments. In the event that electrical connections of the powered surgical devices are compromised during use, measurement signals output by the sensors of the present disclosure remain unaltered. In addition, the sensors are programmable allowing for adjustments to gain and offset values in order to optimize the measurement signals.

With reference to FIG. 1, a powered surgical device 10 includes a handle assembly 20, which is configured for selective connection with an adapter assembly 30, which in turn, is configured for selective connection with an end effector, such as an annular reload 40. Although generally referred to as being a powered surgical device, it is contemplated that the surgical device 10 may be a manually actuated and may include various configurations.

Figure 2:
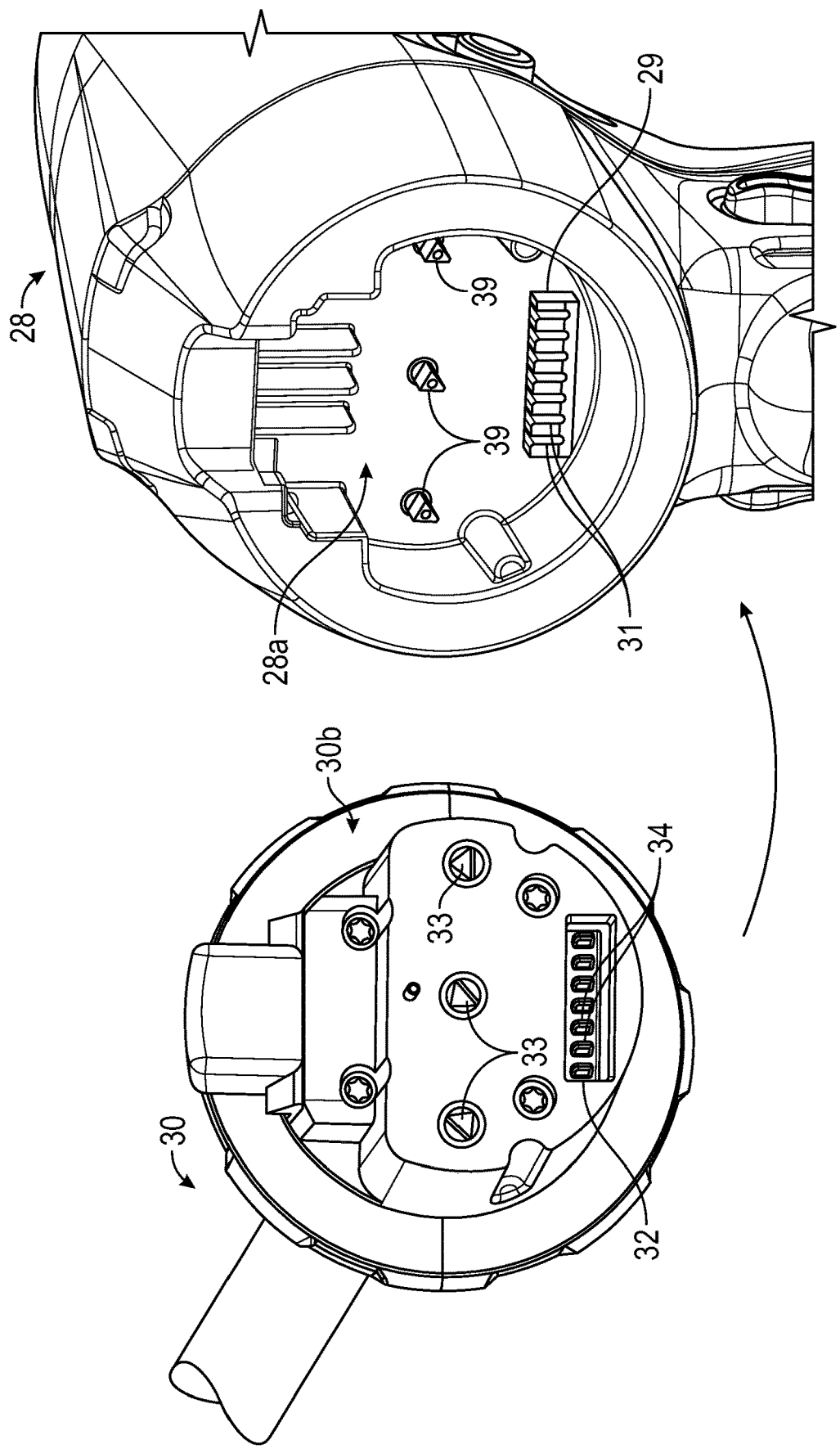
FIG. 2 is a perspective view illustrating a connection of the adapter assembly and the handle assembly of FIG. 1 according to an embodiment of the present disclosure.

The handle assembly 20 includes a handle housing 22 having a lower housing portion 24, an intermediate housing portion 26 extending from and/or supported on a portion of the lower housing portion 24, and an upper housing portion 28 extending from and/or supported on a portion of the intermediate housing portion 26. As shown in FIG. 2, a distal portion of the upper housing portion 28 defines a nose or connecting portion 28a that is configured to accept a proximal end portion 30b of the adapter assembly 30.

Figure 3:
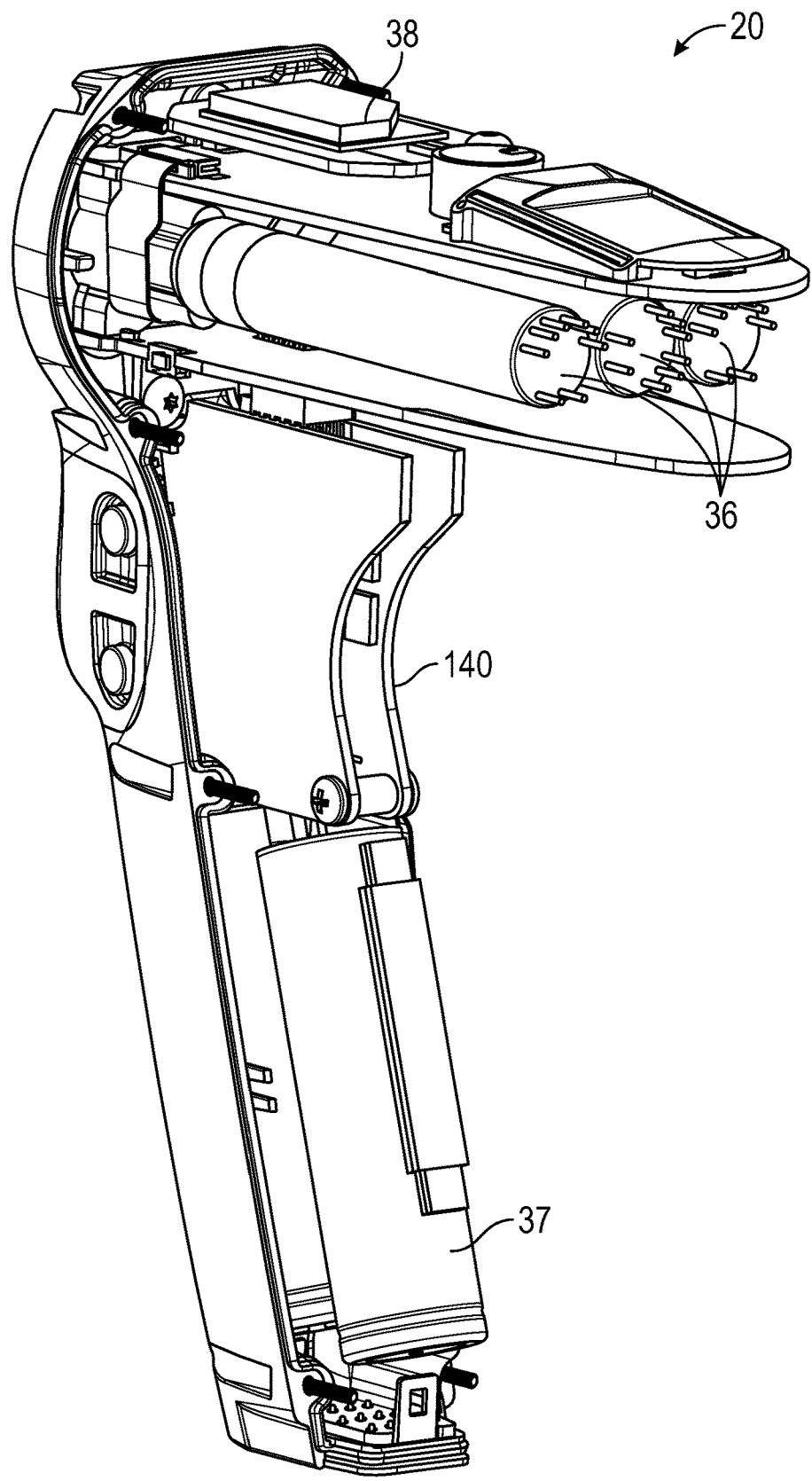
FIG. 3 is perspective view of internal components of the handle assembly according to an embodiment of the present disclosure.

With reference to FIG. 3, the handle assembly 20 includes one or more motors 36 which are coupled to a battery 37. The handle assembly 20 also includes a main controller 38 for operating the motors 36 and other electronic components of the handle assembly 20, the adapter assembly 30, and the reload 40. The motors 36 are coupled to corresponding drive shafts 39 (FIG. 2), which are configured to engage sockets 33 on the proximal end portion 30b, such that rotation of the drive shafts 39 is imparted on the sockets 33. The actuation assembly 52 (FIG. 6B) is coupled to a respective socket 33. The actuation assembly 52 is configured to transfer rotational motion of the sockets 33 into linear motion and to actuate the reload 40 (FIG. 1) along with the anvil assembly 58.

Figure 4:
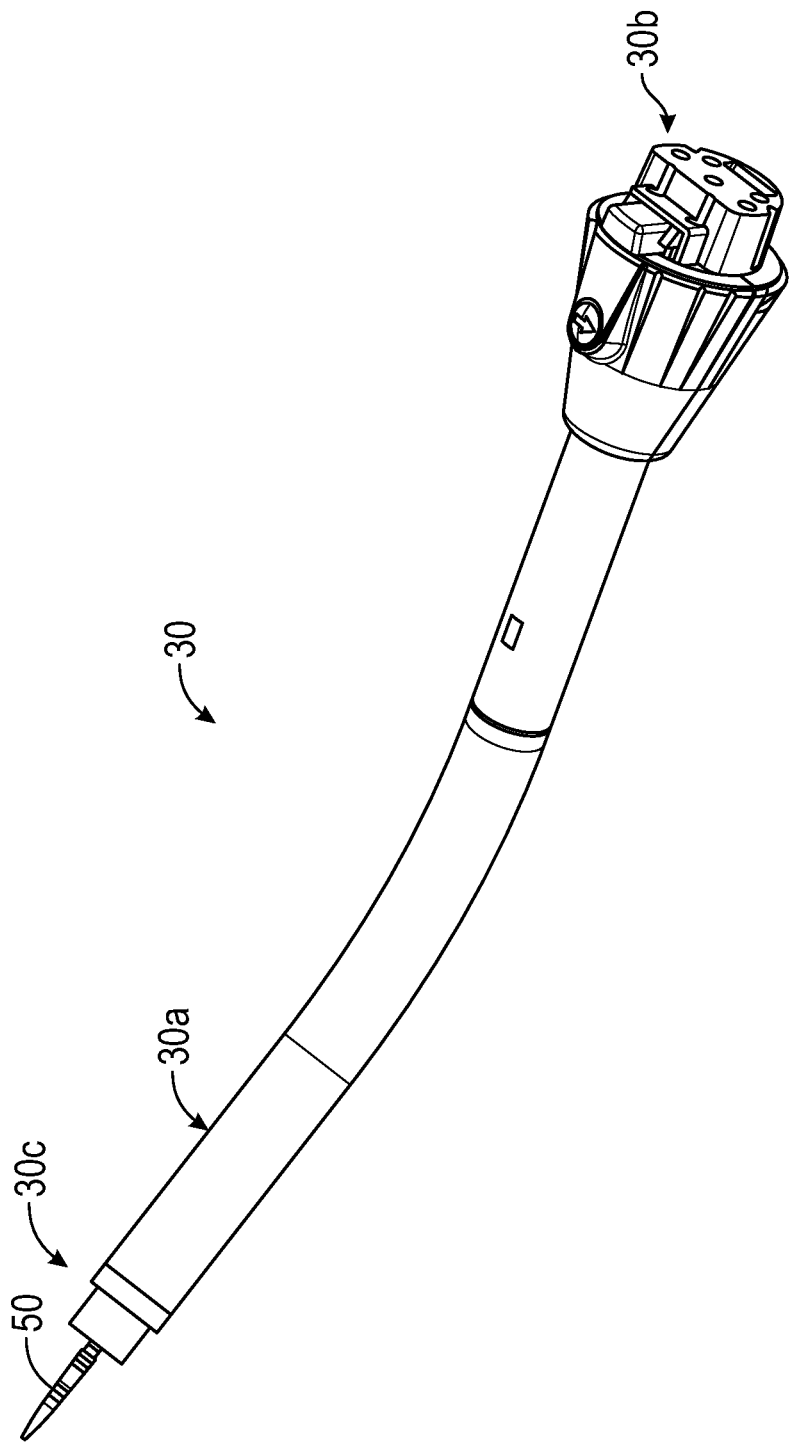
FIG. 4 is a perspective view of the adapter assembly of FIG. 1 without the reload according to an embodiment of the present disclosure.

With reference to FIG. 4, the adapter assembly 30 includes a tubular housing 30a that extends between a proximal end portion 30b that is configured for operable connection to the connecting portion 28a of the handle assembly 20 and an opposite, distal end portion 30c that is configured for operable connection to the reload 40. In this manner, the adapter assembly 30 is configured to convert a rotational motion provided by the handle assembly 20 into axial translation useful for advancing/retracting a trocar member 50 slidably disposed within the distal end portion 30c of the adapter assembly 30 (FIG. 5) for firing staples of the reload 40.

With reference to FIG. 2, the connecting portion 28a includes an electrical receptacle 29 having a plurality of electrical contacts 31, which are in electrical communication with electronic (e.g., main controller 38) and electrical components (e.g., battery 37) of the handle assembly 20. The adapter assembly 30 includes a counterpart electrical connector 32 that is configured to engage the electrical receptacle 29. The electrical connector 32 also includes a plurality of electrical contacts 34 that engage and electrically connect to their counterpart electrical contacts 31.

With reference to FIG. 4, the trocar member 50 is slidably disposed within the tubular housing 30a of the adapter assembly 30 and extends past the distal end portion 30c thereof. In this manner, the trocar member 50 is configured for axial translation, which in turn, causes a corresponding axial translation of an anvil assembly 58 (FIG. 1) of the reload 40 to fire the staples (not shown) disposed therein. The trocar member 50 includes a proximal end which is coupled to the tubular housing 30a of the adapter assembly 30. A distal end portion of the trocar member 50 is configured to selectively engage the anvil assembly 58 of the reload 40 (FIG. 4). In this manner, when the anvil assembly 58 is connected to the trocar member 50, as will be described in detail hereinbelow, axial translation of the trocar member 50 in the first direction results in an opening of the anvil assembly 58 relative to the reload 40, and axial translation of the trocar member 50 in a second, opposite direction, results in a closing of the anvil assembly 58 relative to the reload 40.

Figure 5:
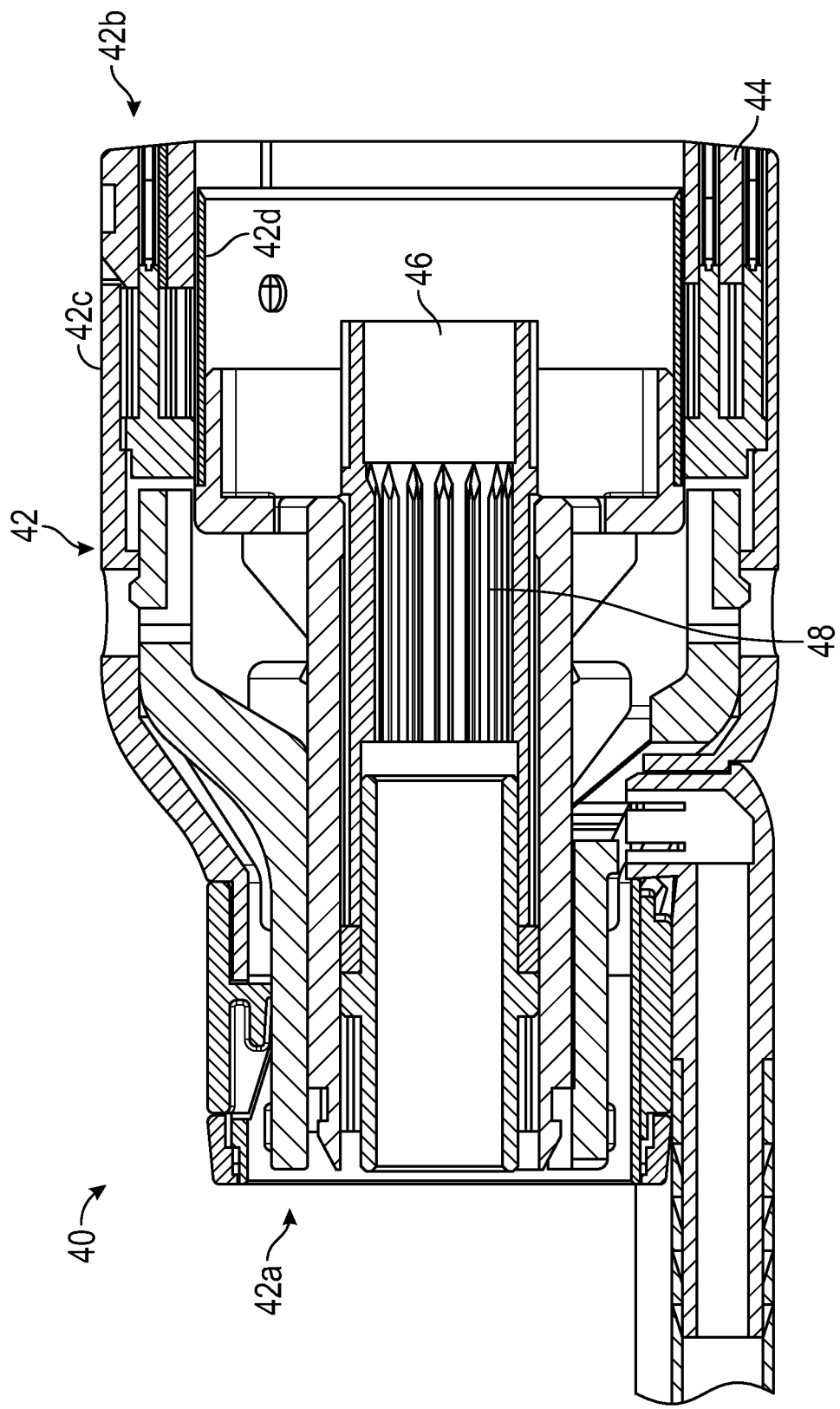
FIG. 5 is a side, cross-sectional view, of the reload of FIG. 1 according to an embodiment of the present disclosure.

As illustrated in FIGS. 1 and 5, the reload 40 is configured for operable connection to adapter assembly 30 and is configured to fire and form an annular array of surgical staples, and to sever a ring of tissue. The reload 40 includes a housing 42 having a proximal end portion 42a and a distal end portion 42b and a staple cartridge 44 fixedly secured to the distal end portion 42b of the housing 42. The proximal end portion 42a of the housing 42 is configured for selective connection to the distal end portion 30c of the adapter assembly 30 and includes a means for ensuring the reload 40 is radially aligned or clocked relative to the adapter assembly 30.

With reference to FIG. 5, the housing 42 of the reload 40 includes an outer cylindrical portion 42c and an inner cylindrical portion 42d. The outer cylindrical portion 42c and the inner cylindrical portion 42d of the reload 40 are coaxial and define a recess 46. The recess 46 of the reload 40 includes a plurality of longitudinally extending ridges or splines 48 projecting from an inner surface thereof which is configured to radially align the anvil assembly 58 relative to the reload 40 during a stapling procedure.

Figure 6A:
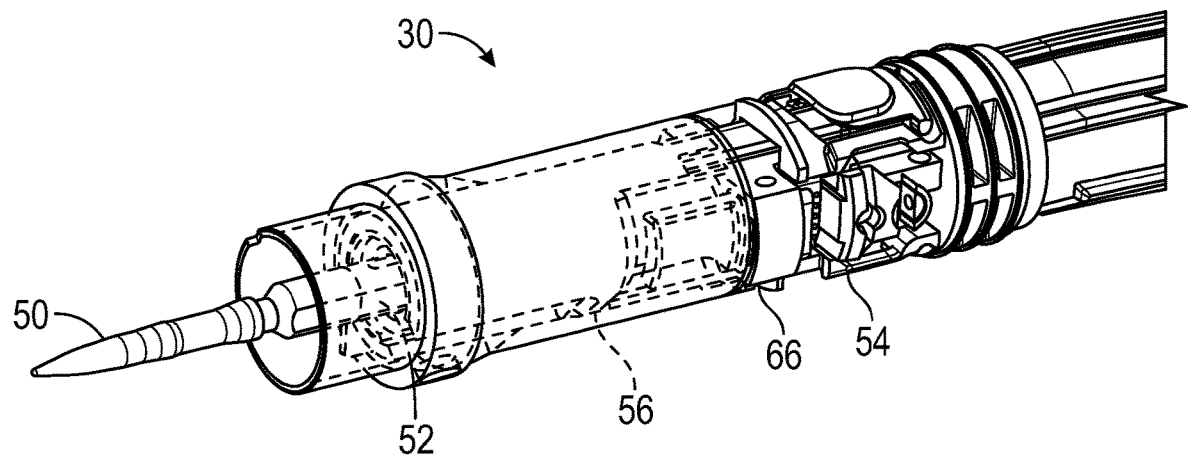
FIG. 6A is a perspective view of the distal end portion of the adapter assembly according to an embodiment of the present disclosure.
Figure 6B:
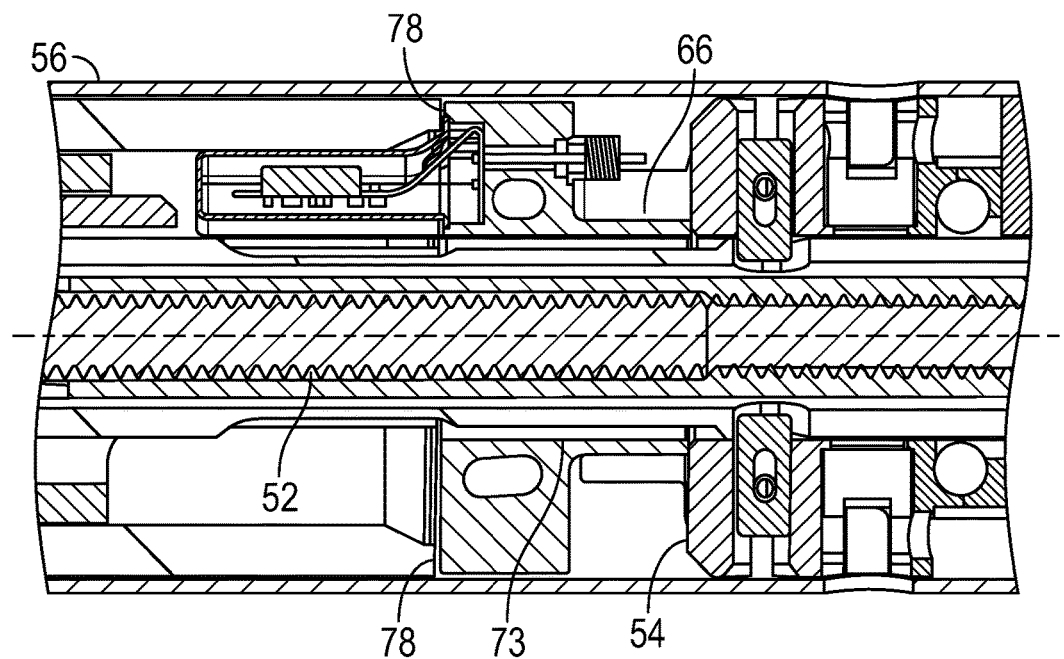
FIG. 6B is a cross-sectional view of the distal end portion of the adapter assembly according to an embodiment of the present disclosure.
Figure 7:
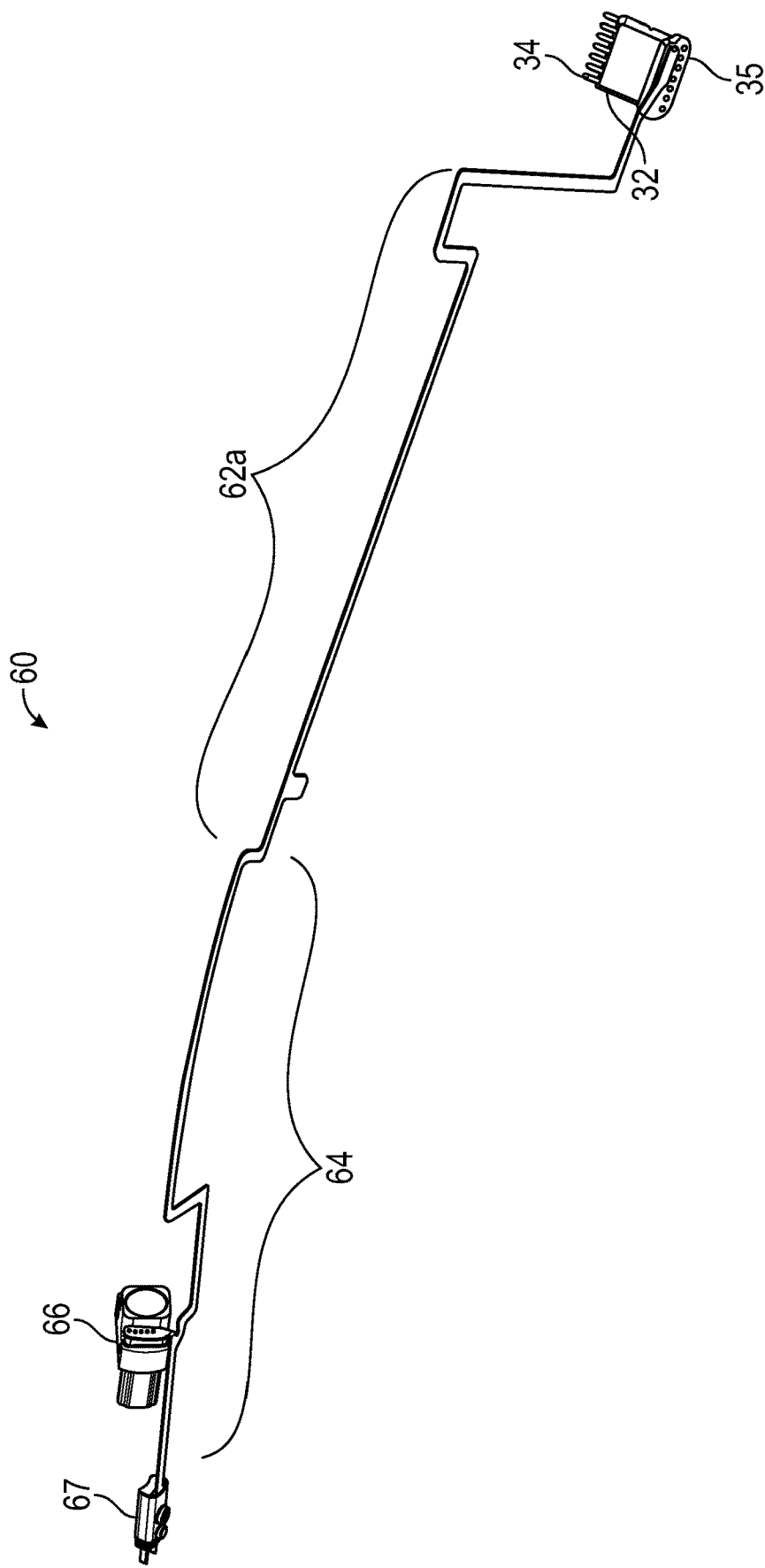
FIG. 7 is a perspective view of an electrical assembly of the adapter assembly of FIG. 1 according to an embodiment of the present disclosure.
Figure 8:
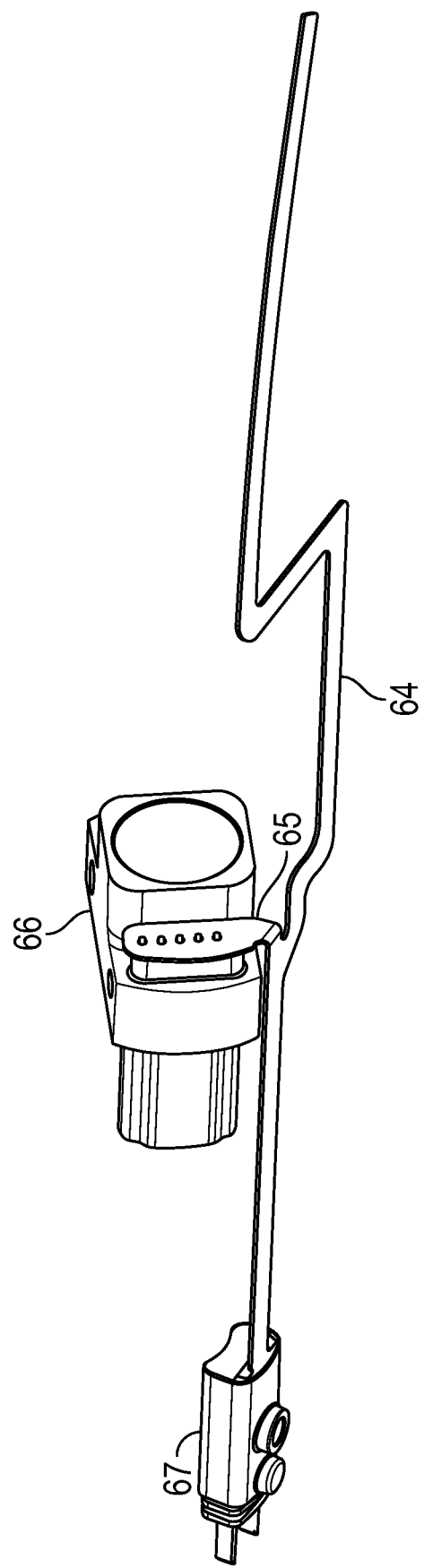
FIG. 8 is a perspective view of a distal portion of the electrical assembly according of FIG. 7 to an embodiment of the present disclosure.
Figure 9:
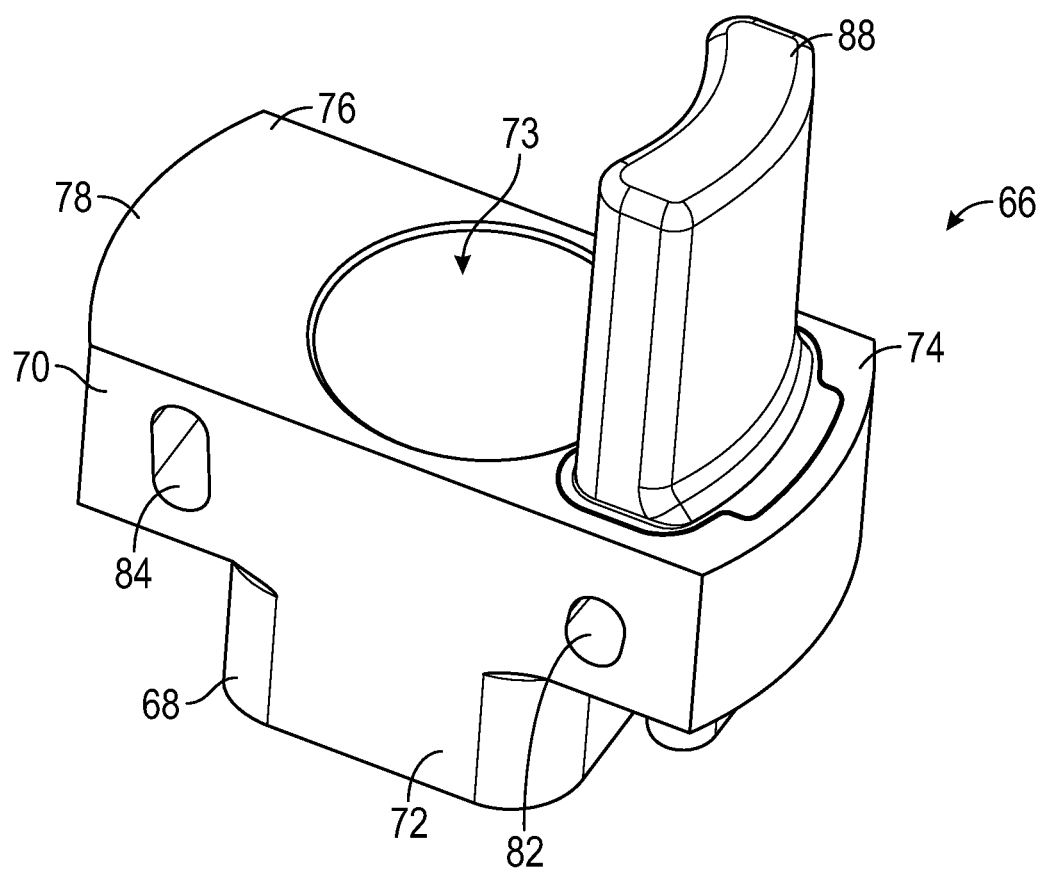
FIG. 9 is a perspective top view of a load sensing assembly of the electrical assembly of FIG. 7 according to an embodiment the present disclosure.
Figure 10:
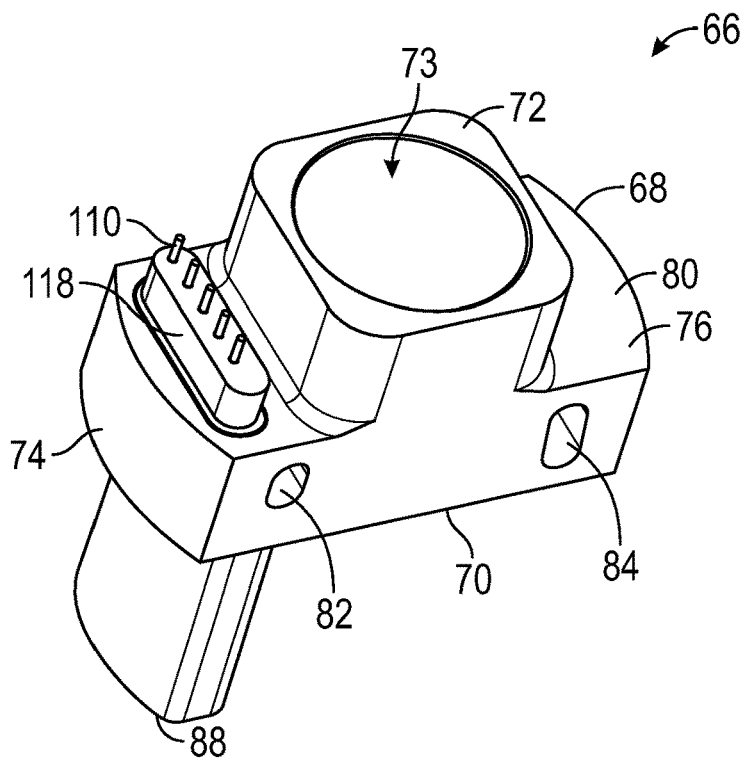
FIG. 10 is a perspective bottom view of the load sensing assembly of FIG. 9.

With reference now to FIGS. 6-8, adapter assembly 30 includes an electrical assembly 60 disposed therewithin, and configured for electrical connection with and between handle assembly 20 and reload 40. Electrical assembly 60 provides for communication (e.g., identifying data, life-cycle data, system data, load sense signals) with the main controller 38 of the handle assembly 20 through the electrical receptacle 29.

Electrical assembly 60 includes the electrical connector 32, a proximal harness assembly 62 having a ribbon cable, a distal harness assembly 64 having a ribbon cable, a load sensing assembly 66, and a distal electrical connector 67. The electrical assembly 60 also includes the distal electrical connector 67 which is configured to selectively mechanically and electrically connect to a chip assembly (not shown) of reload 40.

Electrical connector 32 of electrical assembly 60 is supported within the proximal end portion 30b of the adapter assembly 30. Electrical connector 32 includes the electrical contacts 34 which enable electrical connection to the handle assembly 20. Proximal harness assembly 62 is electrically connected to the electrical connector 32 disposed on a printed circuit board 35.

Load sensing assembly 66 is electrically connected to electrical connector 32 via proximal and distal harness assemblies 62, 64. Load sensing assembly is also electrically connected to distal harness assembly 64 via a sensor flex cable. As shown in FIGS. 6A and 6B, an actuation assembly 52, which is coupled to the trocar member 50, extends through the load sensing assembly 66. The load sensing assembly 66 provides strain measurements imparted on the adapter assembly 30 during movement of the trocar member 50 when coupled to the anvil assembly 58 during clamping, stapling, cutting, and other mechanical actuations.

For a detailed description of an exemplary powered surgical stapler including an adapter assembly and a reload, reference may be made to commonly owned U.S. Patent Application Publication No. 2016/0310134 to Contini et al., titled "Handheld Electromechanical Surgical System," filed Apr. 12, 2016, incorporated by reference hereinabove.

With reference to FIGS. 9-13, the load sensing assembly 66 includes a sensor body 68 having a platform 70 and a tubular portion 72 extending from the platform 70. The sensor body 68 also defines a lumen 73 through the platform 70, thereby separating the platform 70 into a first portion 74 and a second portion 76. The lumen 73 allows for the passage of the actuation assembly 52 therethrough. The sensor body 68 may be formed from any suitable material, such as stainless steel, that allows for the sensor body 68 to be elastically deformed when stressed. In embodiments, the sensor body 68 may be fabricated from stainless steel, such as 17-4 stainless steel heat-treated to H-900 standard.

The platform 70 also includes a top surface 78 and a bottom surface 80 (FIG. 10) as well as a first slot 82 defined within the first portion 74 of the platform 70 and a second slot 84 defined through the second portion 76 of the platform 70. Slots 82 and 84 work in combination with the design of sensor body 68 to provide uniform bending when loaded. The uniform loading and resulting strain output causes a load sensor circuit 86 (FIGS. 11 and 12) of the load sensing assembly 66 to provide provides linear strain output at the first portion 74 of the platform 70, which is measured by a load sensor circuit 86 secured to the first portion 74 and covered by a cover 88 as shown in FIG. 11.

With reference to FIGS. 6A and 6B, the load sensing assembly 66 is disposed between a support block 54 and a connector sleeve 56. In particular, the tubular portion 72 of the sensor body 68 rests on the support block 54 and the top surface 78 of the platform 70 abuts a proximal end of the connector sleeve 56. During operation of the surgical device 10, namely, clamping, stapling, and cutting, the sensor body 68 is elastically deformed (similar to a support beam) in proportion to the forces applied to the support block 54 and the connector sleeve 56. In particular, deflection of the sensor body 68 applies a force to the load sensor circuit 86 (FIGS. 11 and 12), which is deformed causing its electrical resistance to increase, which is reflected in its measurement signal. A change in a baseline of the measurement signal is indicative of the forces being imparted on the support block 54 and the connector sleeve 56, which are generally descriptive of the forces encountered during clamping, stapling, and cutting.

Figure 11:
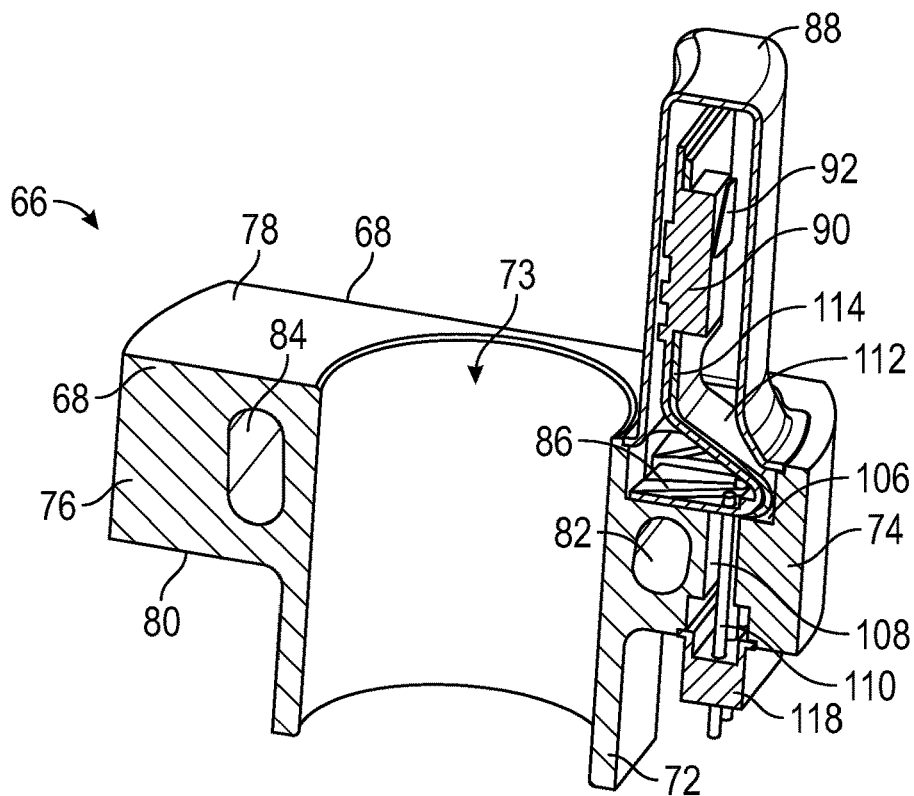
FIG. 11 is a cross-sectional, side view of the load sensing assembly of FIG. 9.
Figure 12:
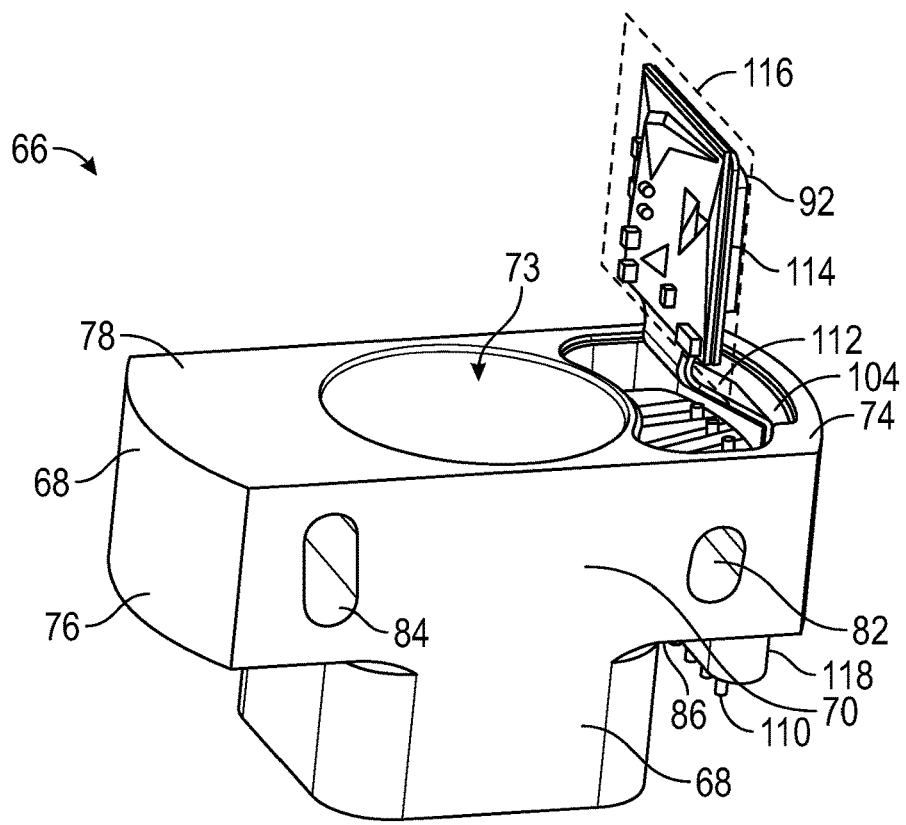
FIG. 12 is a perspective top view of the load sensing assembly of FIG. 8 without a cover.
Figure 16:
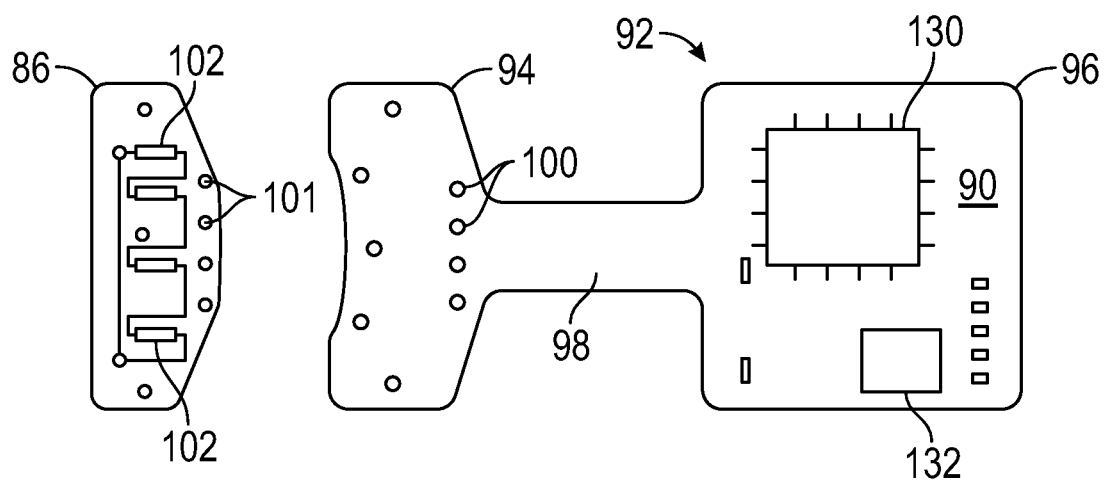
FIG. 16 is a top, schematic view of a load sensor circuit and a signal processing circuit according to an embodiment the present disclosure.

With reference to FIGS. 11, 12, and 16, the load sensor circuit 86 is coupled to a signal processing circuit 90, which includes a flexible circuit board 92 having a contact portion 94 and a signal processing circuit portion 96. The contact portion 94 is interconnected with the signal processing circuit portion 96 via a flex strip 98 and includes a plurality of first pass-through contacts 100. The signal processing circuit 90 includes analog and digital circuit components (e.g., controller 130) that are configured to perform signal processing on signals from the load sensor circuit 86 and output a measurement signal to the handle assembly 20.

The flexible circuit board 92 may be any suitable dielectric multilayer flexible materials, such as PYRALUX® materials available from DuPont of Willmington, Delaware, liquid crystal polymer materials, and the like. In embodiments, the flexible circuit board 92 may include additional dielectric layers, which stiffen the flexible circuit board 92 so that the solder connections of the components located along the flexible circuit board 92 are not subjected to unwanted movement due to thermal expansion and/or mechanical movement of the load sensing assembly 66. In embodiments, the flexible circuit board 92 may fabricated in a flat state (FIG. 16) and formed during soldering to sensor body 68 (FIG. 11). In further embodiments, the flexible circuit board 92 may be pre-bent using a fixture with or without heat to form the desired shape denoted in FIG. 11.

The contact portion 94 is configured to couple to the load sensor circuit 86, which includes one or more load sensing devices 102 interconnected by a plurality traces or other conductors. In embodiments, the load sensing devices 102 may be strain gauges, pressure sensors (e.g., pressure sensing film), or any other suitable transducer devices configured to measure mechanical forces and/or strain and output an electrical signal in response thereto. Signal output is achieved when the load sensing circuit 86 is bonded to the sensor body 68 such that the load sensing devices 102 are positioned in the respective areas of linear strain output when load sensing assembly 66 is elastically deformed.

The load sensor circuit 86 may be a single circuit board, such as a flexible circuit board with the load sensing devices 102 being disposed thereon and electrically interconnected via internal traces. The load sensing devices 102 are also electrically coupled via traces to a plurality of second pass-through contacts 101. In embodiments, the load sensing devices 102 may be attached to the first portion 74 of the platform 70 individually, rather than through the load sensor circuit 86 and then wired together to provide for electrical coupling.

The plurality of load sensing devices 102 may be arranged on the load sensor circuit 86 in a variety of configurations to achieve temperature compensation or other resistor networks, such as a Wheatstone Bridge in which two load sensing devices 102 are arranged to move in response to tension of the load sensing assembly 66 and two load sensing devices 102 are arranged to move in response to compression of the load sensing assembly 66. The configuration of four load sensing devices 102 as shown in FIG. 16 provides maximum signal output and temperature compensation and is known as a full bridge circuit.

Figure 13:
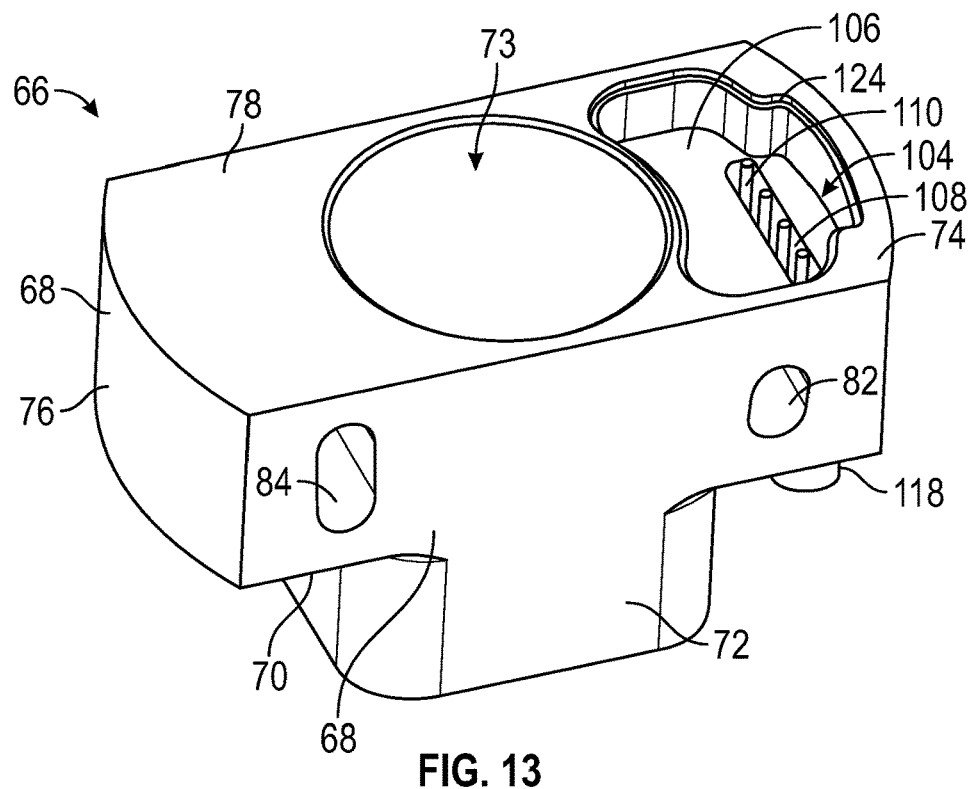
FIG. 13 is a perspective top view of the load sensing assembly of FIG. 8 without a load sensor circuit and a signal processing circuit.

With reference to FIG. 13, the first portion 74 also includes a pocket 104 having a gauging surface 106 for attachment of the load sensor circuit 86 and the contact portion 94 of the signal processing circuit 90. In embodiments, the load sensor circuit 86 may be bonded to the gauging surface 106 such that the signal processing circuit 90 outputs the measurement signal in response to the sensor body 68. The pocket 104 also includes a slot 108 having a plurality of pins 110 passing therethrough.

The slot 108 passes through the pocket 104 to the bottom surface 80 as shown in FIG. 11. The pins 110 are electrically coupled to the signal processing circuit 90 through a plurality of second pass-through contacts 101 (FIG. 16). In particular, when load sensor circuit 86 is bonded to the pocket 104, the second pass-through contacts 101 are inserted over pins 110. Thereafter the first pass-through contacts 100 of the contact portion 94 are also inserted over the pins 110. The first and second pass-through contacts 100 and 101 are aligned such that after soldering of the pins 110 thereto, the signal processing circuit 90 and the load sensor circuit 86 are electrically coupled to the pins 110 and each other. In embodiments, there may be four pins 110, with two of the pins 110 acting as communication lines and the remaining two pins 110 proving electrical power for energizing the load sensor circuit 86 and the signal processing circuit 90. After soldering, the flexible circuit board 92 can be arranged to fit within the cover 88.

In embodiments, the flexible circuit board 92 may be folded and/or bent as shown in FIGS. 11 and 12. In further embodiments, a support structure 112 may be disposed within the pocket 104. The support structure 112 includes one or more surfaces 114 onto which the flexible circuit board 92 is attached. The support structure 112 may have any suitable shape such that the flexible circuit board 92 is conformed to the shape of the support structure 112. The flexible circuit board 92 may be secured to the support structure 112 in any suitable manner, e.g., bonding, fasteners, etc.

In further embodiments, a wrap 116 can be disposed over the flexible circuit board 92 to insulate electronic components of the signal processing circuit portion 96 and prevent short circuits if the flexible circuit board 92 contacts an interior surface of the cover 88. The wrap 116 may be polyimide tape or ionomer resin tape, such as KAPTON® and SURLYN®, respectively, from DuPont of Wilmington, Delaware, shrink-wrap, polyisoprene membranes, low durometer potting compounds, parylene coatings, and other dielectric materials and applications suitable for insulating electronic circuits.

Figure 17:
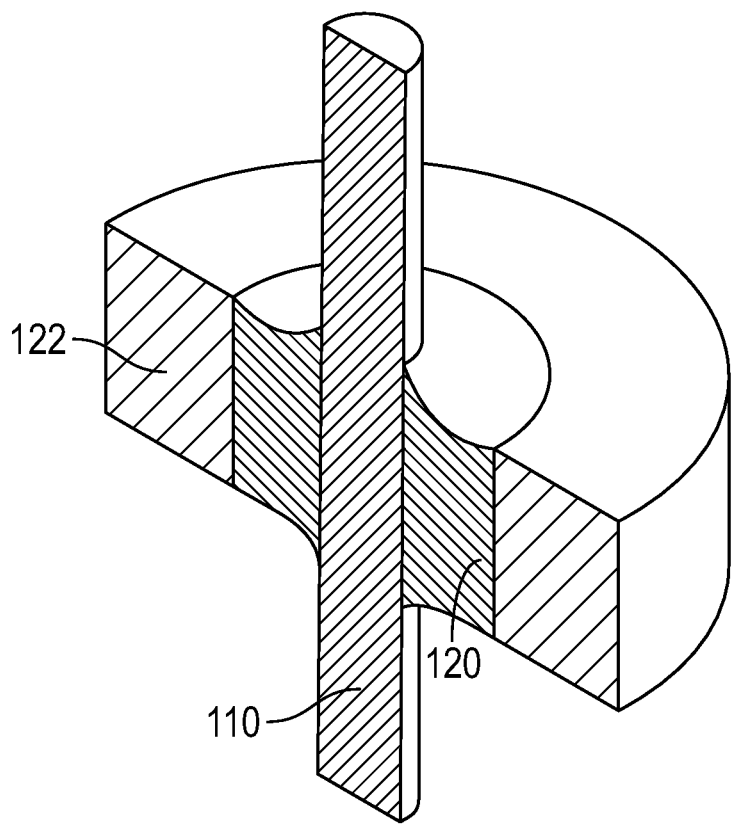
FIG. 17 is a cross-sectional view of a pin connector of the load sensing assembly of FIG. 9 according to an embodiment the present disclosure.

With reference to FIG. 10-13, the pins 110 are secured within a header 118, which hermetically seals the pocket 104 at the bottom surface 80. As shown in FIG. 17, each of the pins 110 is encased in a glass sleeve 120, each of which is then embedded in a peripheral housing 122. This construction seals the interior of cover 88 and the pocket 104 from the outside once the header 118 is bonded to slot 108 at the bottom surface 80 of the platform. The header 118 may be bonded (e.g., welded) to the bottom surface 80.

A hermetic seal may be formed by inserting the pins 110 through their respective glass sleeves 120, after which the pins 110 along with their glass sleeves 120 are inserted into corresponding bores of the peripheral housing 122 of the header 118. The entire assembly of the pins 110, glass sleeves 120, and the peripheral housing 122 are heated. Upon heating, the bore of the peripheral housing 122, which may be formed from any suitable metal (e.g., stainless steel), expands and the glass sleeves 120 fill the void. The pins 110 being formed from metal expand minimally and upon cooling, the glass sleeves 120 provide compression seals about their respective pins 110 and bores of the peripheral housing 122. As shown in FIG. 8, the pins 110 are the coupled to a flex cable 65, which in turn, is coupled to distal harness assembly 64.

Figure 14:
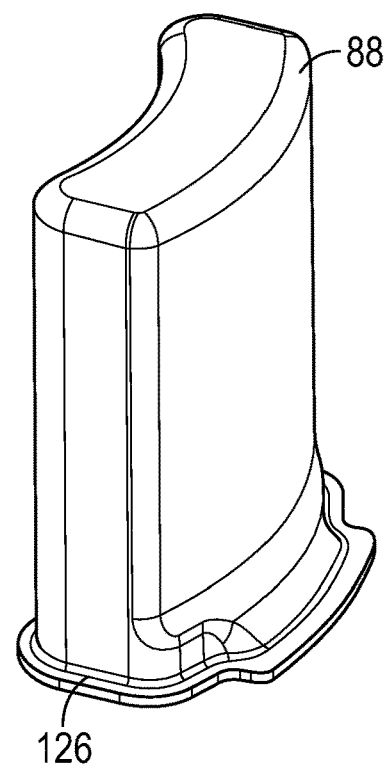
FIG. 14 is a perspective top view of a cover of the load sensing assembly of FIG. 9 according to an embodiment the present disclosure.
Figure 15:
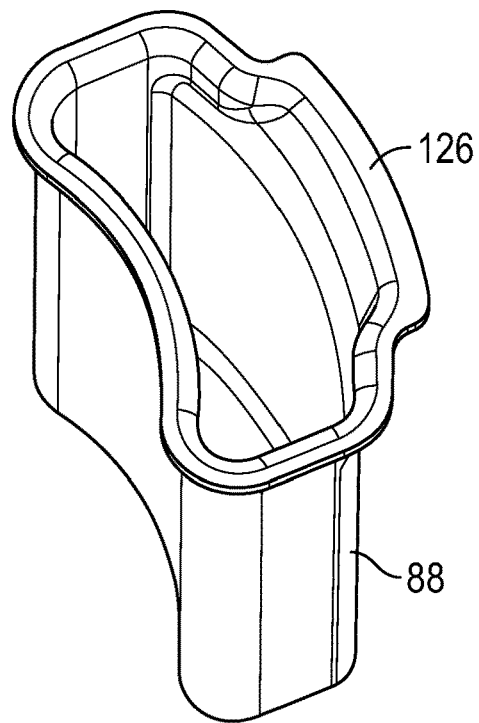
FIG. 15 is a perspective bottom view of the cover of FIG. 14.

With reference to FIG. 13, the pocket 104 further includes a step 124 along an entire perimeter of the pocket 104. The step 124 corresponds in size and shape to a flange 126 of the cover 88 as shown in FIGS. 14 and 15, to allow for creating of a hermetic seal. In addition, the flange 126 is configured to fit within the step 124 and is coplanar with the step 124. This allows for the flange 126 to sit on a flat surface portion of the step 124.

The cover 88 may be formed from a similar material as the sensor body 68. The cover 88 may be secured to the sensor body 68 in any suitable manner to ensure that the signal processing circuit 90 is hermetically sealed within the cover 88. In embodiments, the cover 88 and the sensor body 68 may be formed from a metal, such as stainless steel, and the cover 88 may be welded (e.g., by a laser) to the platform 70 around their respective perimeters. The cover 88 may be manufactured using a deep draw process, which provides for economical manufacturing. In embodiments, the sensor body 68 and the cover 88 may be manufactured using any suitable such as, machining, metal injection molding, 3-D printing, and the like.

Figure 18:
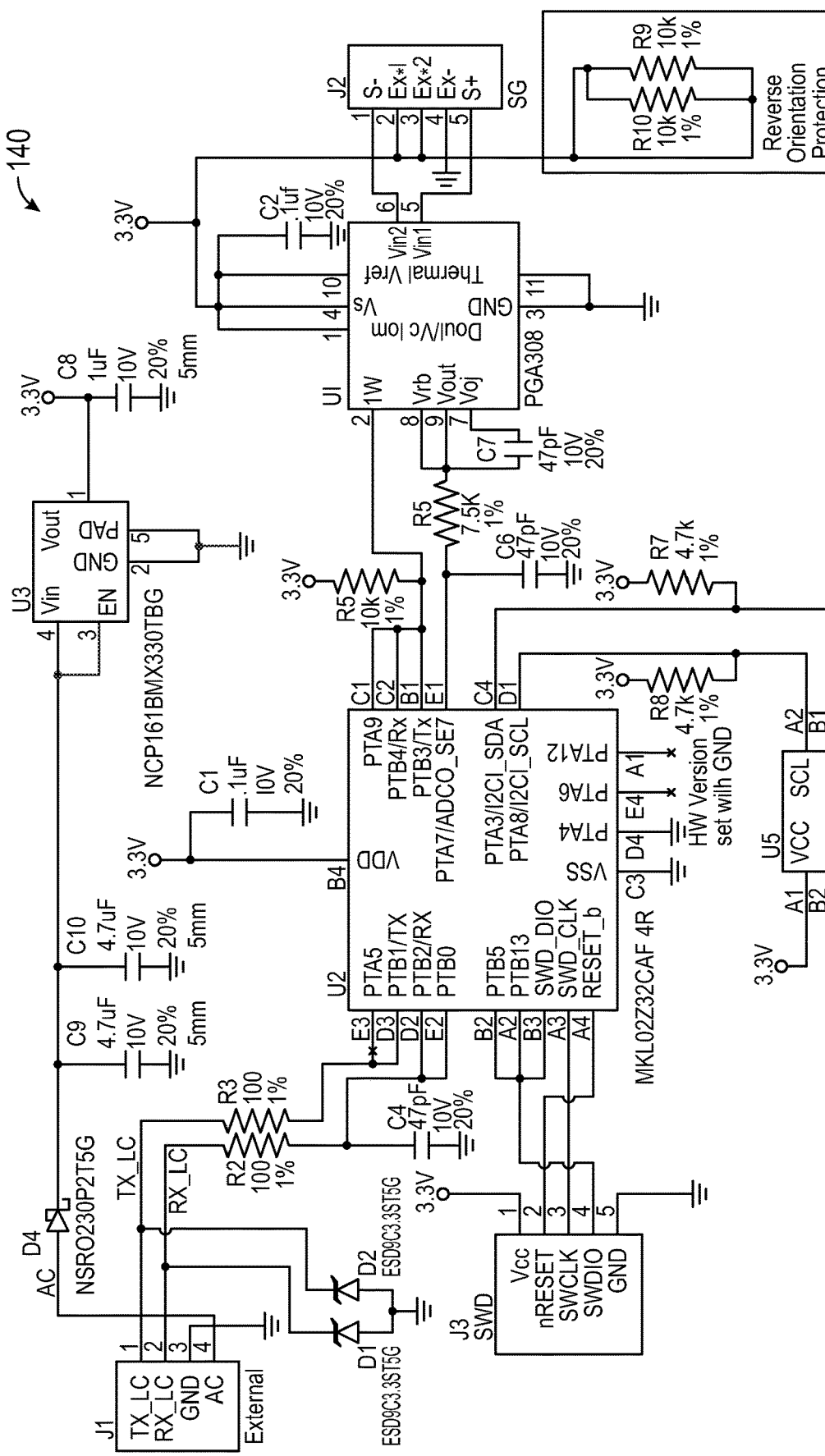
FIG. 18 is an electrical schematic drawing of the signal processing circuit of FIG. 16 according to an embodiment of the present disclosure.

With reference to FIGS. 16 and 18, the signal processing circuit 90 includes a controller 130 having a storage device 132, which may be an electrically erasable programmable read-only memory ("EEPROM") or any other suitable non-volatile memory device. The controller 130 may be any suitable microcontroller or any other processor, such as CORTEX® microcontrollers available from ARM of Cambridge, UK. The controller 130 may include analog-to-digital converters, digital-to-analog converters, timers, clocks, watchdog timers, and other functional components that enable the controller 130 to process the analog measurement signals from the load sensing devices 102. In particular, the controller 130 is configured to amplify the signal from the load sensing devices 102 of the load sensor circuit 86, filter the analog signal, and convert the analog signal to a digital signal. The controller 130 is also configured to transmit the digital signal to the main controller 38 of the handle assembly 20, which controls operation of the surgical device 10 based on the digital signal indicative of the sensed mechanical load.

The controller 130 is programmable to allow for adjustments to gain and offset parameters for processing the analog signal. In particular, the controller 130 stores a zero balance value and corresponding gain and offset parameters in the storage device 132. After assembly of the load sensing assembly 66, load sensor circuit 86 is calibrated. In embodiments, the load sensor circuit 86 may be recalibrated periodically to ensure accurate measurements. Calibration may be performed under zero balance, namely, when the load sensor circuit 86 is unloaded. If the load sensor circuit 86 is outputting any signal even in an unloaded state, or conversely, not outputting a sufficient signal in response to a loaded state, the controller 130 is programmed to compensate for such discrepancy. This is accomplished by adjusting gain and offset parameters of the controller 130, which allows the controller 130 to adjust the analog signal to correspond to the zero balance state. The controller 130 may be programmed through the main controller 38, which is coupled to the controller 130 through the pins 110 as described above.

It will be understood that various modifications may be made to the embodiments of the presently disclosed adapter assemblies. Therefore, the above description should not be construed as limiting, but merely as exemplifications of embodiments. Those skilled in the art will envision other modifications within the scope and spirit of the present disclosure.

What is claimed is:

1. A load sensing assembly comprising:
   a sensor body including a pocket defined therein;
   a load sensor circuit disposed within the pocket and coupled to the sensor body;
   a signal processing circuit disposed within the pocket and electrically coupled to the load sensor circuit; and
   a cover disposed over the pocket and hermetically enclosing the load sensor circuit and the signal processing circuit therein.

2. The load sensing assembly according to claim 1 further comprising:
   a header including a contact coupled to the load sensor circuit and the signal processing circuit, wherein the header is coupled to the sensor body thereby forming a hermetic seal therebetween.

3. The load sensing assembly according to claim 1, wherein the sensor body further includes a slot defined therein, the slot being connected to the pocket.

4. The load sensing assembly according to claim 1, wherein the load sensing assembly includes a strain gauge.

5. The load sensing assembly according to claim 1, wherein the signal processing circuit includes a flexible circuit board.

6. The load sensing assembly according to claim 5, wherein the signal processing circuit is covered by a dielectric wrap.

7. An adapter assembly comprising:
   a tubular housing having a proximal end portion and a distal end portion;
   an actuation assembly; and
   a load sensing assembly disposed with the tubular housing, the load sensing assembly configured to measure a load exerted on the tubular housing, the load sensing assembly including:
   a sensor body including a pocket defined therein;
   a load sensor circuit disposed within the pocket and coupled to the sensor body;
   a signal processing circuit disposed within the pocket and electrically coupled to the load sensor circuit; and
   a cover disposed over the pocket and hermetically enclosing the load sensor circuit and the signal processing circuit therein.

8. The adapter assembly according to claim 7, wherein the load sensing assembly includes a strain gauge.

9. The adapter assembly according to claim 7, wherein the signal processing circuit includes a flexible circuit board.

10. The adapter assembly according to claim 7, wherein the sensor body includes a lumen defined therethrough and the actuation assembly is movable through the lumen.

11. The adapter assembly according to claim 7, wherein the sensor body further includes a slot defined therein, the slot being connected to the pocket.

12. The adapter assembly according to claim 11, wherein the load sensing assembly further includes a header including a contact coupled to the load sensor circuit and the signal processing circuit and the header is coupled to the sensor body thereby forming a hermetic seal therebetween.

13. The adapter assembly according to claim 12, further comprising:
   an electrically conductive lead coupled to the contact; and
   an electrical connector disposed at the proximal end portion and coupled to the electrically conductive lead.

14. A surgical device including:
   a handle assembly including a controller;
   an adapter assembly including:
      a tubular housing having a proximal end portion configured to couple to the handle assembly and a distal end portion;
      a load sensing assembly disposed with the tubular housing, the load sensing assembly configured to measure a load exerted on the tubular housing, the load sensing assembly including:
         a sensor body including a pocket defined therein;
         a load sensor circuit disposed within the pocket and coupled to the sensor body;
         a signal processing circuit disposed within the pocket and electrically coupled to the load sensor circuit; and
         a cover disposed over the pocket and hermetically enclosing the load sensor circuit and the signal processing circuit therein; and
   a surgical end effector configured to couple to the distal end portion of the adapter assembly.

15. The surgical device according to claim 14, wherein the load sensing assembly includes a strain gauge.

16. The surgical device according to claim 14, wherein the signal processing circuit includes a flexible circuit board.

17. The surgical device according to claim 14, wherein the adapter assembly further includes an actuation assembly including a trocar member and wherein the sensor body includes a lumen defined therethrough and the actuation assembly is movable through the lumen.

18. The surgical device according to claim 14, wherein the sensor body further includes a slot defined therein, the slot being connected to the pocket.

19. The surgical device according to claim 18, wherein the load sensing assembly further includes a header coupled to the sensor body thereby forming a hermetic seal therebetween, the header having a contact coupled to the load sensor circuit and the signal processing circuit.

20. The surgical device according to claim 19, wherein the adapter assembly further includes:
an electrically conductive lead coupled to the contact; and
an electrical connector disposed at the proximal end portion and coupled to the electrically conductive lead.

21. The surgical device according to claim 20, wherein the handle assembly includes an electrical receptacle configured to couple to the electrical connector and the controller is coupled to the electrical receptacle.

* * * * *